US012364569B2

(12) United States Patent
Kitahara et al.

(10) Patent No.: US 12,364,569 B2
(45) Date of Patent: Jul. 22, 2025

(54) MULTI-VIEWPOINT VIDEO CAPTURING DEVICE

(71) Applicant: University of Tsukuba, Tsukuba (JP)

(72) Inventors: Itaru Kitahara, Tsukuba (JP); Tatsuya Oda, Tsukuba (JP)

(73) Assignee: University of Tsukuba, Tsukuba (JP)

( * ) Notice: Subject to any disclaimer, the term of this patent is extended or adjusted under 35 U.S.C. 154(b) by 416 days.

(21) Appl. No.: 17/906,833

(22) PCT Filed: Mar. 24, 2021

(86) PCT No.: PCT/JP2021/012162
§ 371 (c)(1),
(2) Date: Sep. 20, 2022

(87) PCT Pub. No.: WO2021/193697
PCT Pub. Date: Sep. 30, 2021

(65) Prior Publication Data
US 2023/0363852 A1 Nov. 16, 2023

(30) Foreign Application Priority Data
Mar. 26, 2020 (JP) .................................. 2020-055921

(51) Int. Cl.
*A61B 90/00* (2016.01)
*A61B 90/35* (2016.01)
(Continued)

(52) U.S. Cl.
CPC .............. *A61B 90/37* (2016.02); *A61B 90/35* (2016.02); *A61B 90/50* (2016.02); *G06T 7/85* (2017.01);
(Continued)

(58) Field of Classification Search
CPC ......... A61B 90/35; A61B 90/37; A61B 90/50; A61B 2090/367; A61B 2090/371; A61B 2090/502; G06T 7/85; H04N 13/246
See application file for complete search history.

(56) References Cited

U.S. PATENT DOCUMENTS

2011/0264078 A1 10/2011 Lipow et al.
2015/0141759 A1* 5/2015 Charles .............. A61B 17/0218
600/201

FOREIGN PATENT DOCUMENTS

JP 2015-521913 A 8/2015
JP 2017-068810 A 4/2017
(Continued)

OTHER PUBLICATIONS

Yamada (Computer English Translation of Japanese Patent No. JP 2012-120812 A, pp. 1-13. (Year: 2012).*
(Continued)

*Primary Examiner* — Daniel G Mariam
(74) *Attorney, Agent, or Firm* — Banner & Witcoff, Ltd.

(57) ABSTRACT

An imaging lighting instrument for an operation is disposed in a space between an operator's head and a patient, thereby configuring a multi-viewpoint video capturing device for a surgical operation in which blocking of a light by the operator's head or body and appearance of the head in a video are avoided. The imaging lighting instrument includes a plurality of cameras and a plurality of lights attached to a hollow ring-shaped or arc-shaped housing made of a wire member of a finite length, which is devised so as not to interfere with the visual field or work of the operator. Furthermore, the multi-viewpoint video capturing device is configured to have a function of estimating the context of the plurality of cameras and make it possible to perform operation support/recording of a direct-view surgical operation by using a multi-viewpoint video by adding a video information
(Continued)

processing function for selecting a camera video in which an operators' hand or surgical instruments less appear in an image.

2 Claims, 28 Drawing Sheets

(51) Int. Cl.
*A61B 90/50* (2016.01)
*G06T 7/80* (2017.01)
(52) U.S. Cl.
CPC ... *A61B 2090/367* (2016.02); *A61B 2090/371* (2016.02); *A61B 2090/502* (2016.02)

(56) References Cited

FOREIGN PATENT DOCUMENTS

| | | |
|---|---|---|
| JP | 2019-003320 A | 1/2019 |
| JP | 2019-042199 A | 3/2019 |
| WO | 2014004717 A2 | 1/2014 |

OTHER PUBLICATIONS

May 25, 2021—(WO) International Search Report—App PCT/JP2021/012162.

* cited by examiner

102

102

MULTI-VIEWPOINT VIDEO CAPTURING DEVICE

CROSS-REFERENCE TO RELATED APPLICATIONS

This application is a U.S. National Stage application under 35 U.S.C. § 371 of International Application PCT/JP2021/012162 (published as WO/2021/193697 A1), filed Mar. 24, 2021, which claims the benefit of priority to Application JP 2020-055921, filed Mar. 26, 2020. Benefit of the filing date of these prior applications is hereby claimed. Each of these prior applications is hereby incorporated by reference in its entirety.

TECHNICAL FIELD

The present invention relates to a multi-viewpoint video capturing device used for surgical operations, dissections, and the like.

BACKGROUND ART

Some basic surgical operations are direct-view operations performed over a wide operation area under laparotomy and thoracotomy, and are reliable operation methods in which various unexpected situations can be handled even in a surgical operation with a high level of difficulty. However, the current situation is that surgeons perform such direct-view operations based on only information they see with their own eyes, and this method has hardly improved in the history of a modern surgical operation that has continued for more than 100 years.

Comparing a direct-view operation to flying an airplane, modern surgeons are still like a pilot flying an airplane on a long-haul flight with visual flight rules without any support. In this sense, the field of surgical operations is regarded as a field for which information technology (IT) is not up to date.

On the other hand, in recent years, an endoscopic surgical operation in which an endoscope is inserted into the abdomen or chest of a patient and a video of the endoscope is displayed on a large screen monitor for a surgical operation has rapidly become widespread. In an endoscopic surgical operation, information from one clear magnified image can be shared by all participating members, which contributes to an improvement in safety. In addition, since it is possible to easily record and archive videos that capture the center of an operation part, it also contributes greatly to creating surgical teaching materials for surgical education, allowing retrospective learning by young surgeons and students.

In recent years, indications for laparoscopic operations have expanded dramatically, and although this has allowed many high-level operations to be performed, there is also a risk of problems being caused in operation methods performed using inconvenient instruments while viewing a partially enlarged operation part image. For this reason, direct-view operations still continue to play a central role in surgical operations.

Consequently, there is a strong demand for technology development that effectively provides IT information in a direct-view operation, which is a basic surgical operation.

In the related art, video capturing in a direct-view operation has been widely performed on one video camera disposed above the head of an operator. However, videos have been often blocked by an operator's peering motion, or the operator's body such as the head or the shoulder, and there have been many situations in which effective videos could not be captured. In order to solve this problem, it was necessary to allocate at least one staff member to be in charge of video-capture, and to perform imaging by frequently adjusting the position of a camera to a gap between the heads of a plurality of operators.

However, even when such an effort is made, it is not possible to completely avoid the interruption of a video due to an operator's peering. Further, in large hospitals where human resources are relatively generous, it is also possible to allocate such personnel for a special direct-view operation intended for imaging, but it is not possible to easily perform imaging in all daily operations. Further, in most cases at present, it is impossible to perform effective operation video recording of direct-view operations in city hospitals or the like with few personnel.

In a direct-view operation, if caregivers and observers outside an operation field (anesthesiologists, nurses, medical students, or the like) could also see the operation field seen from an operator's line of sight, they could enjoy the benefits of sharing the operation field like in a laparoscopic operation. However, until now, there has been no video equipment system that can achieve this.

As one countermeasure, many attempts have been made to attach a small camera to the operator's head or glasses to image the operator's line of sight. However, in actual clinical practice, the irregular movement of an operator's head causes much blurring on a screen, and thus in reality it is not possible to capture an image readily allowing observation.

Further, an operator often performs viewing while concentrating on only an extremely narrow operation field, but it is effective for the operator to perform a surgical operation while referring to an image of the operation field viewed over a wide field of view in a bird's eye view and an image of the operation field viewed from the opposite viewpoint of the operator in terms of improving the safety of the surgical operation.

However, until now, operators could not view an operation field image from the viewpoint other than that of his or her line of sight. In addition, providing video information to an operator other than that from white light by applying a technique that uses far-infrared rays in addition to white light to highlight cancer lesions and lymph nodes injected with ICG fluorescent dyes and to allow visualization of blood vessels will also be an important function in surgical support devices in the near future.

Patent Document 1 discloses a camera system with a high probability of being able to display medical treatment, the conditions of an affected area to be treated, and the like on a screen by avoiding interference with a field of view of a camera by the peering motion an operator's head, an operator's hands, surgical instruments, or the like at the time of imaging medical treatment such as a surgical operation.

In the technique disclosed in Patent Document 1, a camera mechanism with a shadowless lamp including a plurality of light sources is disposed above the head of an operator. The camera mechanism with a shadowless lamp includes one central camera and a plurality of peripheral cameras, and is configured to image an operation part to be illuminated simultaneously from a plurality of viewpoints.

Further, in the technique disclosed in Patent Document 1, a monitoring mechanism is provided, and a necessary video is selected from among a plurality of videos captured by the central camera and the plurality of peripheral cameras and is displayed on a display device.

In addition, Patent Document 2 discloses a technique for capturing a video of a blood vessel using infrared light and a cold mirror, or a hot mirror.

In recent years, a technique for synchronously imaging a certain scene by a plurality of cameras and generating an image (free viewpoint image) in which scenery seen from any viewpoint (virtual viewpoint) is reproduced has been developed, and for example, highlight scenes and the like of soccer and basketball can be viewed from various angles.

CITATION LIST

Patent Document

Patent Document 1: JP 2019-42199 A
Patent Document 2: JP 2017-68810 A
Patent Document 3: JP 2019-3320 A

SUMMARY OF INVENTION

Technical Problem

In order to apply a multi-viewpoint video technique to a direct-view operation, there are problems that are completely different from those in a multi-viewpoint free video technique that is used in sports games, and the like are being watched. A difference is that an imaging environment in a stadium and an imaging environment in an operating room differ greatly in the positional relationship between a subject, a camera, and an observer.

In the stadium, an observer, that is, a viewer, is not present on a straight line connecting a subject, that is, a player and a camera, and there is no shield.

On the other hand, in a direct-view operation, a surgeon who is an observer always exists between a camera installed above the head and an operation part which is a subject. The surgeon's head, shoulders, or the like are a first shield, and the surgeon's hand or surgical instruments operating directly above an operation field are a second shield, which makes it impossible to obtain images of the subject which are synchronized from a plurality of cameras.

Patent Document 1 is an example in which a multi-viewpoint video is applied to a surgical operation without sufficient consideration of the above-described blocking problem in a direct-view operation. Since a camera mechanism with a shadowless lamp described here is extremely large and is disposed above the surgeon's head, many of the plurality of cameras installed are blocked by the surgeon's head, and it is difficult to effectively image an operation part. Consequently, similar to a case where a direct-view operation is imaged by one camera in the related art, it is difficult to obtain a meaningful image unless a staff member specializing in camera image-capturing is allocated and the position of the camera is continuously adjusted.

Further, it is difficult to obtain an effective video from a plurality of cameras which is a large number of cameras sufficient to obtain a multi-viewpoint video because many of the plurality of cameras are blocked by a surgeon's head, shoulder, or the like and become ineffective.

On the other hand, an essential element in performing a surgical operation is a lighting device that illuminates an operation field. A shadowless lamp in which a plurality of lights are installed is designed such that literally a shadow is expected not to be generated. However, in practice, lighting using a large shadowless lamp as disclosed in Patent Document 1 is often blocked by a surgeon's head, shoulder, or the like, and an effective amount of light does not reach an operation field. As a result, there is a need to frequently adjust the position of a lighting device by the surgeon himself or herself or an external assistant during a surgical operation.

In this manner, in equipment of the related art, including a plurality of camera mechanisms with a shadowless lamp above the head, it was difficult to effectively perform the display and recording of a video image of an operation field without a staff member specializing in camera photographing. In addition, it was not possible to apply an IT technique of a multi-viewpoint video, which has recently progressed dramatically in watching of sports games and the like, to a surgical operation field.

A method of generating a free-viewpoint video includes a technique related to a method of estimating geometric information such as the position and shape of a subject, for example, as disclosed in Patent Document 3. However, in order to generate a free-viewpoint video which is meaningful for a surgical operation, geometric information alone is not sufficient, and it is also necessary to acquire meaningful context information and generate a presentation video based on the information.

Thus, even when the above-described first problem that a video or lighting is blocked by the head or body of an operator has been solved, a second shield such as an operator's hand or a surgical instrument is necessarily present immediately above a subject, and thus it is not possible to obtain an effective multi-viewpoint video. That is, in order to apply a multi-viewpoint video technique to a surgical site, it is necessary to have a function of determining conditions of an imaging scene, that is, estimating context information and automatically selecting a camera video which is not interfered with by an operator's hand and a surgical instrument in accordance with video information, based on the context information.

Further, in a situation in which the present device is applied in real time for operation navigation, the present technique is an effective technique for improving the safety of an operation if a video from another viewpoint, which cannot be perceived from an operator's viewpoint, can be presented to the operator.

For this, it is necessary to have a function of making it possible to automatically recognize a limited narrow region that the operator is gazing at within a wide imaging range. In addition, it is necessary to have a function of determining and presenting an effective image to be presented to the operator except for the region that the operator is gazing at.

An object of the present invention is to provide a multi-viewpoint video capturing device capable of displaying and recording an image of an operation field which is not blocked by the head or body of an operator and not interfered with by the operator's hand and a surgical instrument without excess or deficiency, instead of disposing a camera staff member specializing in imaging.

That is, an object of the present invention is to solve a first problem that a video and lighting are blocked by the head or body of an operator, which could not be solved by an existing device, by devising the shape of equipment and devising the position of the equipment disposed, and a further object of the present invention is to solve a second blocking problem due to an operator's hand or a surgical instrument by a video information processing technique, and to apply a multi-viewpoint video capturing technique to a surgical operation field.

On the other hand, in the multi-viewpoint video capturing device of the present invention, the shape, size, and arrangement of the multi-viewpoint video capturing device must not interfere with an operator's line of sight or interfere with work.

Solution to Problem

In order to solve the above-described problems, a multi-viewpoint video capturing device according to an embodiment of the present invention includes an imaging instrument including a plurality of cameras attached to a circular ring-shaped or an arc-shaped housing made of a wire member of a finite length and aimed toward a subject being a target for work performed by an operator, and a fixing instrument configured such that the imaging instrument is disposed at a position between the operator's top of the head and the subject.

As a preferred embodiment of the present invention, the multi-viewpoint video capturing device further includes a camera calibration processing unit configured to estimate camera parameters including positions, postures, and focal lengths of the plurality of cameras attached to the imaging instrument, based on imaging information of the subject imaged by the plurality of cameras, and a presentation viewpoint gaze point determination processing unit configured to detect a gaze point, which is a region of the subject perceived by a surgeon, in multi-viewpoint image data, estimate three-dimensional coordinate information of the gaze point with reference to the camera parameters, and select one or a plurality of cameras that will perform imaging with the gaze point in an optimal state based on the three-dimensional coordinate information.

Further, a lighting environment that is not blocked by an operator's head or shoulder by disposing a plurality of lights between the plurality of cameras attached to the housing is also provided.

Advantageous Effects of Invention

According to the present invention, it is possible to continue capturing a clear operation field image under a lighting environment which is not blocked by the head or body of an operator without disposing a camera staff member specializing in imaging. Further, it is also possible to have a medical treatment support function of providing detailed operation field information received from viewpoints other than a surgeon's viewpoint to the surgeon in real time by having a function of effectively capturing the center of an operation field that an operator is gazing at from multiple viewpoints, which can contribute to an improvement in the safety of a direct-view operation. In addition, recording such a clear operation field image provides highly reliable storage of image operation records.

Such medical information records have an extremely high value and also can be expected to contribute greatly to surgical education. Further, in operations performed at hospitals in areas where there are few medical staff members and there is a shortage of doctors, a clear operation field image can be obtained without a staff member for imaging, and thus it is also possible to expect an application for improving the safety of remote medical treatment, such as transmission of the operation field image to a skilled surgeon at a remote location in real time to receive advice.

In addition, as described later, in a third modification example, a doctor with a camera in a laparoscopic operation is unnecessary, and it is possible not only to achieve efficiency in personal resources but also to contribute to an improvement in safety by providing a wide multi-viewpoint video rather than a narrow field of vision in the related art.

A plurality of lighting sources installed in a multi-viewpoint video capturing device according to an embodiment of the present invention are never blocked by the head or body of a surgeon by the features of the present device which is installed at a position below the head of a surgeon, and a shadowless environment having no shadow can be provided to an operation field. Further, the multi-viewpoint video capturing device is equipped with light sources having different wavelengths such as infrared light and ultraviolet rays, and thus it is possible to provide many pieces of information that cannot be recognized by the naked eye of the surgeon.

Problems, configurations, and effects other than those described above will become apparent by the following description of an embodiment.

DESCRIPTION OF EMBODIMENTS

Multi-Viewpoint Video Capturing Device

Figure 1A:
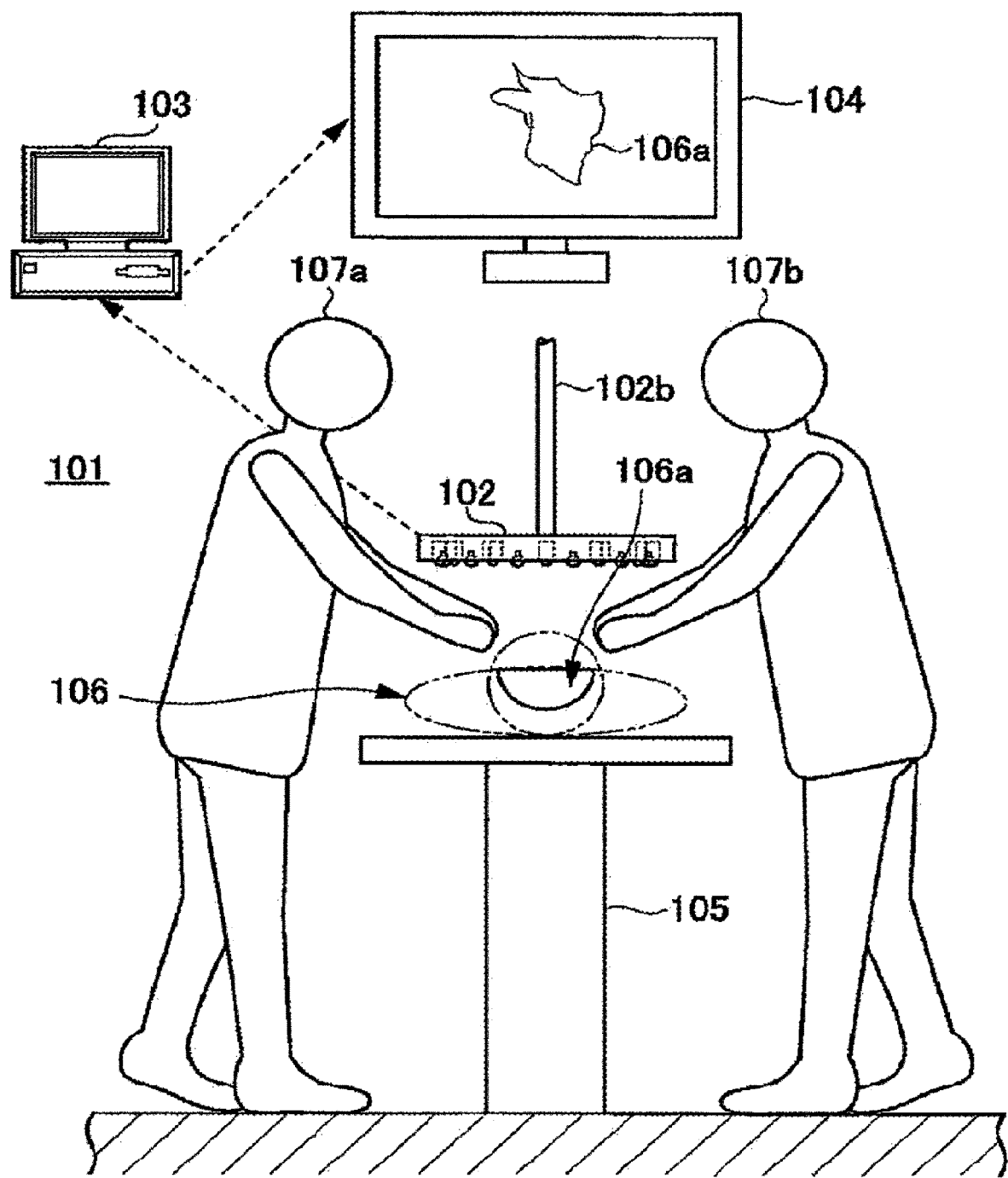
FIGS. 1A-1B is a schematic view illustrating the state of use of a multi-viewpoint video capturing device according to an embodiment of the present invention, and is a diagram illustrating the state of use of an imaging lighting instrument when viewed from above.
Figure 1B:
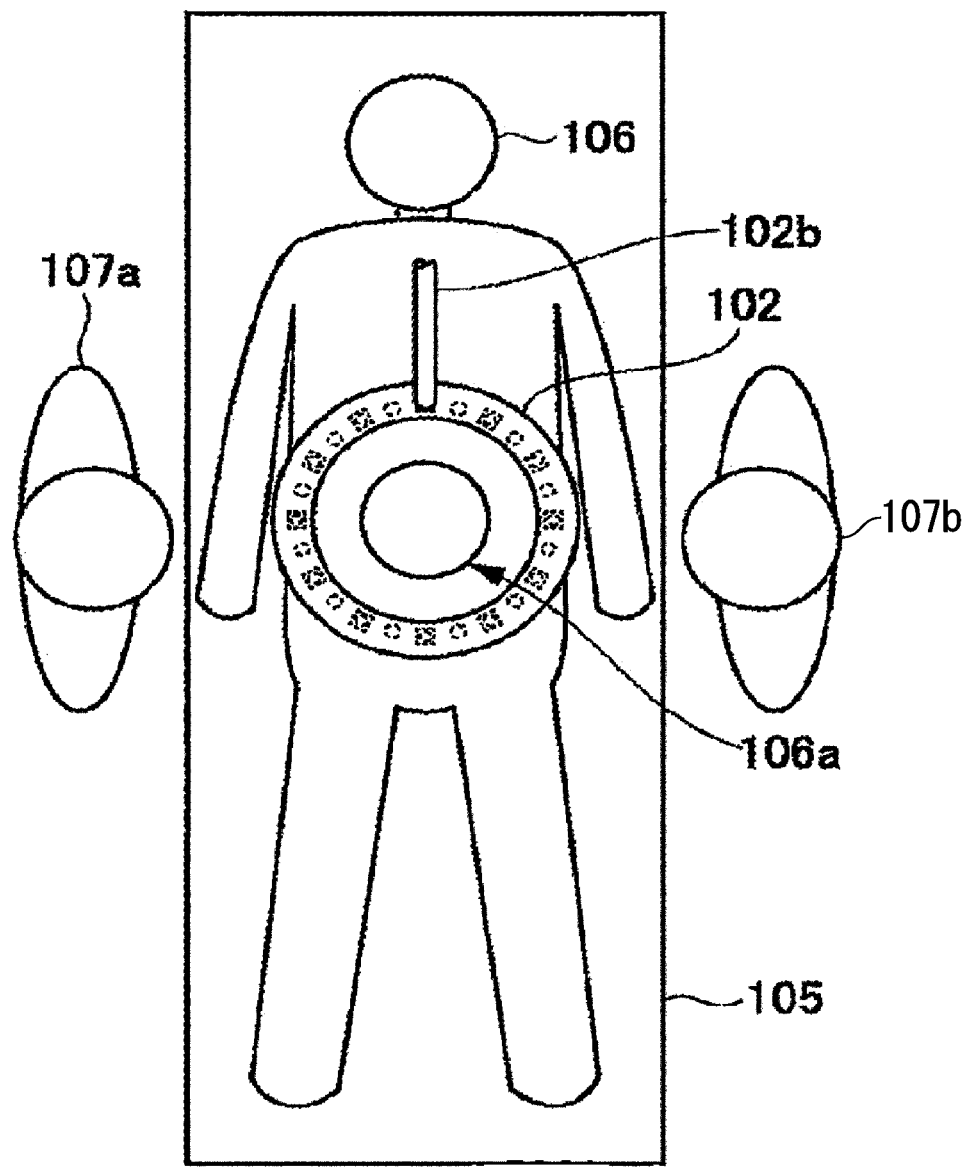

FIG. 1A is a schematic view illustrating the state of use of a multi-viewpoint video capturing device 101 according to an embodiment of the present invention, and FIG. 1B is a diagram illustrating the state of use of an imaging lighting instrument 102.

As illustrated in FIG. 1A, the multi-viewpoint video capturing device 101 includes the imaging lighting instrument 102 and a video lighting processing device 103 connected to the imaging lighting instrument 102. Further, a large-screen external monitor 104 is connected to the video lighting processing device 103.

A patient 106 under anesthesia and with an incision in the abdomen is laid on an operating table 105. A surgeon 107a performs an operation on the patient 106, and a surgeon 107b assists the surgeon 107a. That is, the surgeon 107a is a surgeon performing the operation, and the surgeon 107b is an assistant. Hereinafter, the surgeon 107a and the assistant 107b are collectively described as a "surgeon 107".

The horizontal width of the operating table 105 is approximately 50 cm. The dissected abdomen, that is, an operation field 106a, has an opening of approximately 20 cm on the short side and a depth of approximately 10 cm.

As illustrated in FIGS. 1A and 1B, the hollow ring-shaped imaging lighting instrument 102 is installed at a position approximately 40 cm apart from the center of the operation field 106a in an upward direction. In the imaging lighting instrument 102, a plurality of cameras (see FIG. 2B) and a plurality of lights (see FIG. 2B) are installed toward the operation field 106a in a circular or elliptical ring-shaped housing in the example of FIG. 1. As a result, the cameras and lights do not interfere with the fields of vision of the surgeons 107a and 107b when visually recognizing the operation field 106a.

The surgeon 107 peeps at the operation field 106a through a hollow portion of the imaging lighting instrument 102 and inserts his or her hand into a space of approximately 40 cm below the imaging lighting instrument 102 to perform operation work. In order to secure a space for performing such operation work, the imaging lighting instrument 102 is suspended from a structure (for example, a ceiling) above the operation field by, for example, a fixing instrument 102b and is disposed between the head of the surgeon and the operation field 106a.

The surgeon 107 can visually recognize the operation field 106a to peep at the operation field 106a through the hollow portion of the imaging lighting instrument 102, but can also perform an operation and operation assistance using a space between the imaging lighting instrument 102 and the operation field 106a while referring to a video of the operation field 106a displayed on the external monitor 104.

In a direct-view operation of the related art, an area 60 cm directly above an operation part is widely recognized in the field of surgical medical treatment as a sacred area that cannot be accessed, and it was an area in which there was hesitancy in developing and disposing new medical equipment. That is, operation monitoring in a direct-view operation has been performed entirely by viewing the operation field 106a with the naked eye of the surgeons 107a and 107b performing an operation, and thus the arrangement of any object at the area 60 cm directly above the operation part has been recognized as interference with the field of vision of the surgeon 107.

The imaging lighting instrument 102 used in the multi-viewpoint video capturing device 101 according to the embodiment of the present invention is an instrument disposed within the area 60 cm directly above the operation part which is a taboo region. However, the surgeon 107 can visually recognize an operation field to peep at the ring-shaped device installed in the hollow, while the surgeon 107 can perform operation work without a delay because a sufficient working space is secured between the present device and an affected area. In addition, it is possible to continue capturing a clear operation field image under a lighting environment which is not blocked by the head and shoulder of the surgeon 107.

A large number of cameras provided ion the imaging lighting instrument 102 are disposed surrounding the operation field 106a. Thus, it is possible to image the operation field 106a from various directions during an operation.

In the related art, in order to image the operation field 106a from various directions, the cameras are moved in necessary directions each time. In the case of the imaging lighting instrument 102 that constitutes a portion of the multi-viewpoint video capturing device 101 according to the embodiment of the present invention, a function of physically moving the individual cameras is not required. By electronically switching between videos obtained by the plurality of cameras previously disposed surrounding the operation field 106a as necessary, it is possible to easily acquire a video in an imaging direction required by the surgeon 107.

A video captured by the camera of the imaging lighting instrument 102 can be viewed on the external monitor 104 installed in the vicinity of the operating table 105. The surgeon 107 can view the operation field 106a with the naked eye and also check the operation field 106a on the large-screen external monitor 104.

Further, as indicated by the name, the multi-viewpoint video capturing device 101 can form a video from a free viewpoint based on videos obtained from the plurality of cameras. Thus, the operation field 106a which is a subject can be viewed in a three-dimensional manner by switching the cameras to move viewpoints.

Overall Image of Imaging Lighting Instrument 102

Figure 2A:
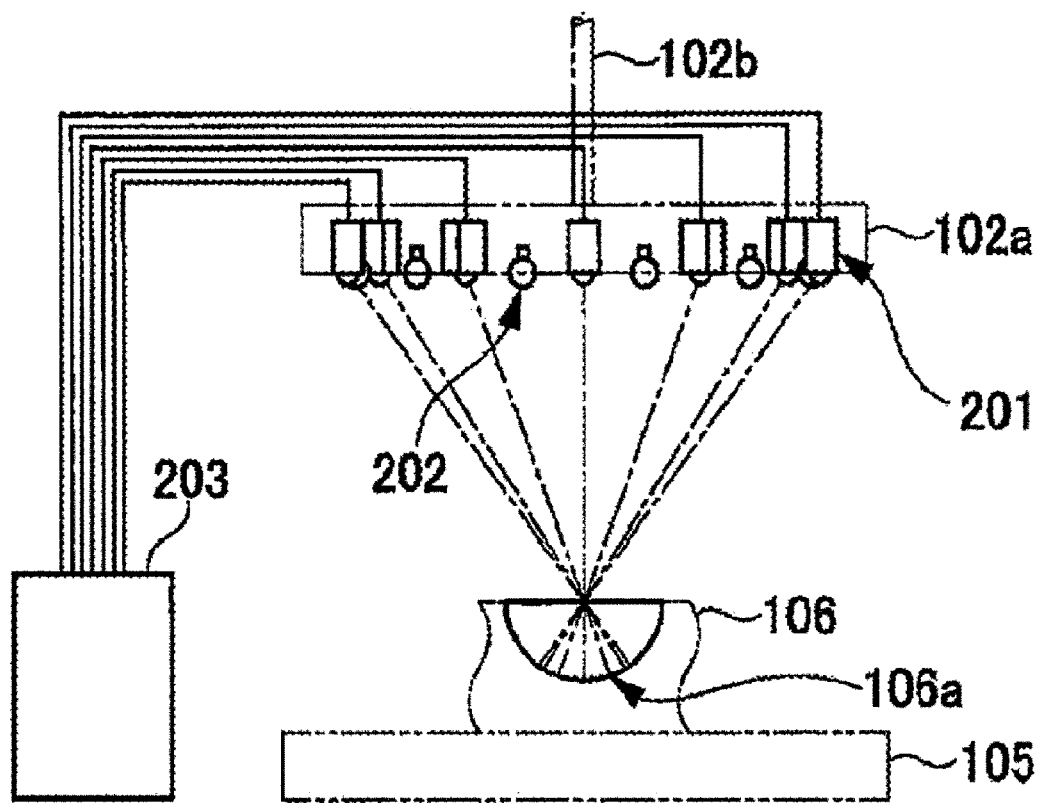
FIGS. 2A-2C is a transparent side view, a bottom view, and a transparent perspective view of the imaging lighting instrument.
Figure 2B:
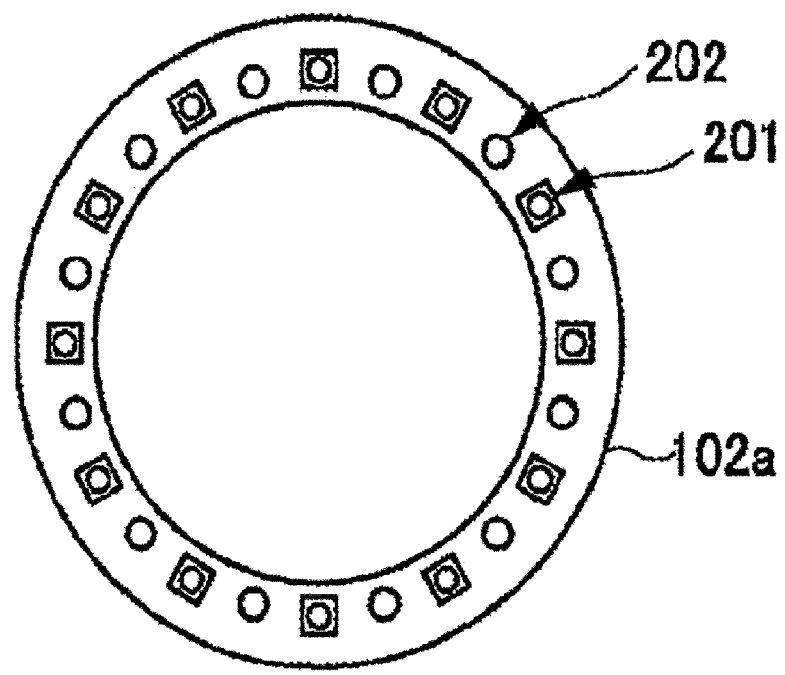
Figure 2C:
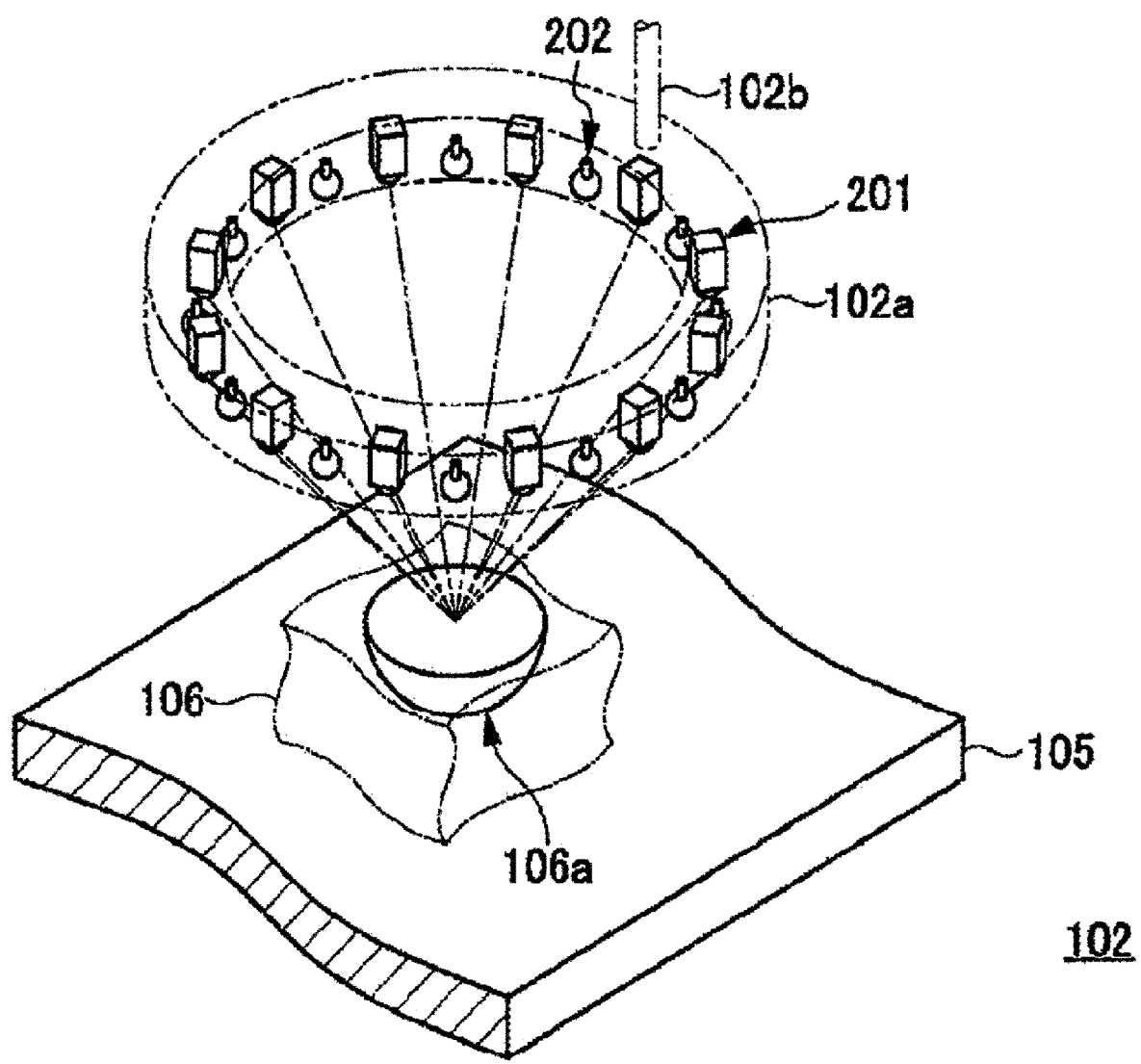

FIG. 2A is a transparent side view of the imaging lighting instrument 102, FIG. 2B is a bottom view of the imaging lighting instrument 102 when viewed from the bottom, and FIG. 2C is a transparent perspective view of the imaging lighting instrument 102.

The imaging lighting instrument 102 includes a housing 102a having a hollow circle or elliptical ring shape and the fixing instrument 102b. The fixing instrument 102b is provided in the imaging lighting instrument 102 in order to dispose and fix the housing 102a of the imaging lighting instrument 102 at a position between the operation field 106a, which is a subject, and the head of the surgeon 107 which is an operator.

As illustrated in FIGS. 2A, 2B, and 2C, the circular housing 102a has a size of, for example, 30 to 40 cm. Since the housing 102a has a hollow shape, the surgeon 107 can directly view the operation field 106a with the naked eye through the hollow portion of the housing 102a.

The thickness of the housing 102a is preferably as thin as possible so as not to interfere with the field of vision of the surgeon 107. Since an imaging element has been miniaturized in recent years, the housing 102a may be formed of a thin pipe, and the imaging element may be accommodated in the pipe. In addition, an imaging element of, for example, approximately 1 cm may be fixed to the outside of a pipe and fastened. In this configuration, the pipe has such a thickness that cannot accommodate the imaging element.

That is, the surgeon 107 can also view the operation field 106a through the external monitor 104, in addition to directly viewing the operation field 106a with the naked eye in a direct-view operation. The existence of a plurality of means for observing the operation field 106a leads to a psychological sense of relief for the surgeon 107 and contributes to an improvement in safety.

In order not to interfere with the field of vision of the surgeon 107, the ring-shaped housing 102a is preferably as thin as possible, and it is essential that the fixing instrument 102b does not intervene between the imaging lighting instrument 102 and the operation field 106a so as not to interfere with an operation and operation assistance.

As illustrated in FIGS. 2A and 2B, for example, 36 cameras 201 and 36 lights 202 are alternately disposed in the housing 102a. The cameras 201 and the lights 202 are disposed toward the operation field 106a as illustrated in FIG. 2C.

In a case where the shape of the housing 102a is a perfect circular shape, and the number of cameras 201 is 36, each of the cameras 201 captures a video so as to surround the operation field 106a within a range of 10 degrees.

That is, the cameras 201 are disposed in the housing 102a at predetermined intervals, and all of the cameras 201 are disposed toward the operation field 106a. For this reason, the cameras 201 are disposed in the housing 102a so as to have different imaging angles with respect to the operation field 106a which is a subject.

However, when the number of cameras 201 is large, the cameras 201 are disposed side by side without gaps between the cameras 201. Even in such a case, the cameras 201 are disposed in the housing 102a with different imaging angles with respect to the operation field 106a which is a subject.

As described above, the imaging lighting instrument 102 is disposed within the area 60 cm directly above the operation field 106a which is a subject. Thus, the cameras 201 disposed in the housing 102a are at distances extremely close to the subject, which leads to a state where the imaging angles of all of the cameras 201 are necessarily different from each other.

Although it is only required that the number of cameras 201 and the number of lights 202 are determined arbitrarily, it is preferable that 36 or more cameras 201 be ideally disposed to obtain a high-resolution multi-viewpoint video. When the angle between the cameras 201 is approximately 10 degrees, the surgeon 107, who is viewing a video captured by the camera 201, can get a view by smoothly switching between videos. When the angle between the cameras 201 is approximately 15 degrees or more, the surgeon 107, who is viewing a video captured by the camera 201, can clearly switch between videos but may feel uncomfortable when switching between videos is performed.

As the camera 201, it is desirable to use an ultra-small imaging element capable of capturing a high-definition color video, such as an imaging element that has been used in, for example, smartphones in recent years. Each camera 201 includes an interface such as a USB interface, and is connected to the video lighting processing device 103 illustrated in FIG. 1 via a USB hub 203.

As a light source used in the light 202, it is desirable to use, for example, a high-brightness LED that emits three primary colors with high color reproducibility. In general, LEDs have directivity, and thus it is desirable to appropriately disperse light toward the operation field 106a which is a subject by sealing the housing 102a with an acrylic plate or vinyl chloride plate that has been made opaque by smoke processing, sandblasting, or the like.

Note that the light source used in the light 202 is not limited to an LED, and for example, a krypton sphere may be adopted, or an LED and a krypton sphere may be mixed in order to improve color reproducibility.

Figure 3:
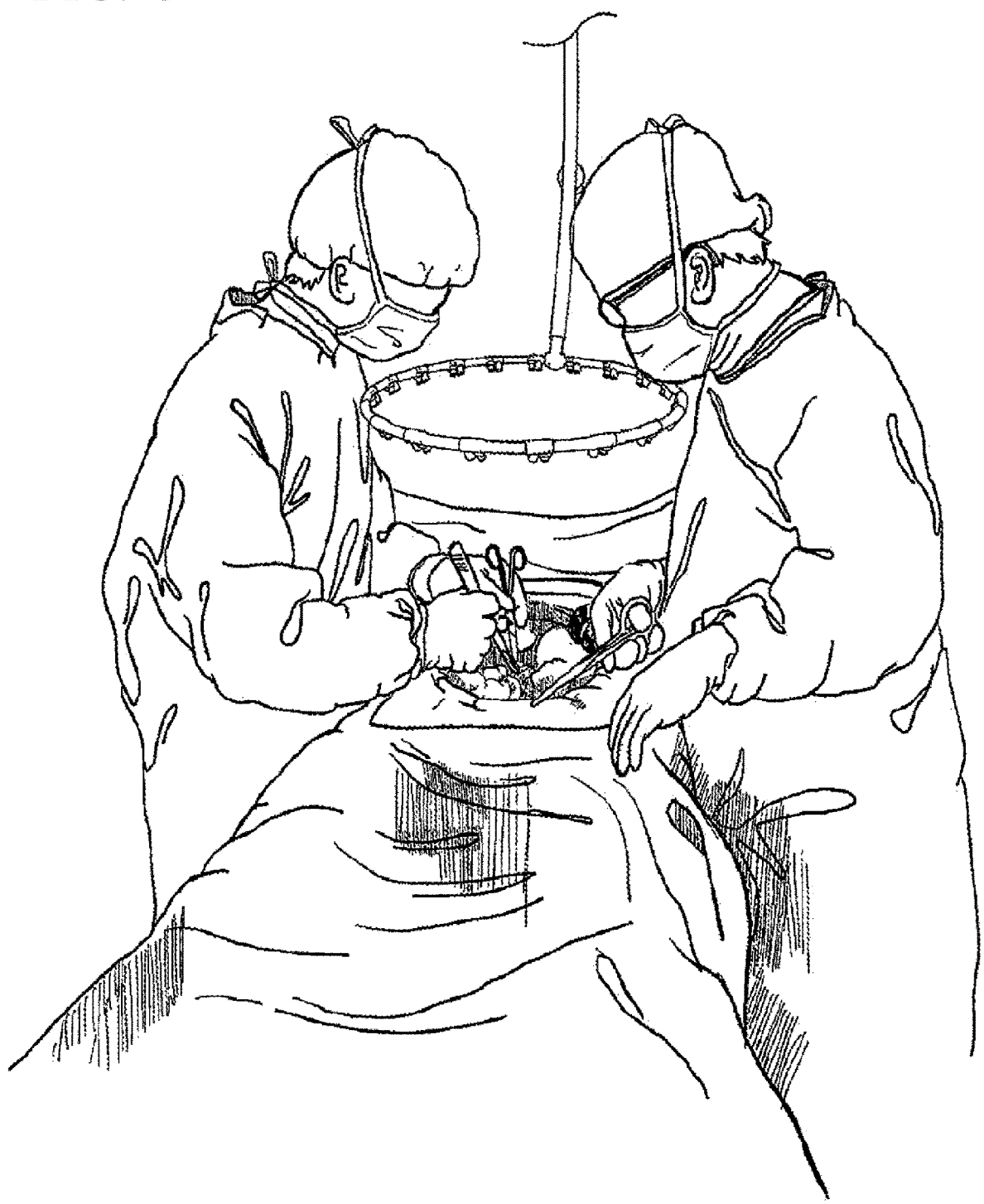
FIG. 3 is a simulation diagram of the state of use of a hollow ring type multi-viewpoint video capturing device in an operating room.

FIG. 3 is a simulation diagram illustrating a state where the ring-shaped imaging lighting instrument 102, which is the basic type, is used in the operating room. The surgeon 107 observes the operation field by peeping at the operation field through a ring formed by the housing 102a of the imaging lighting instrument 102, and performs an operation using a working space of approximately 40 cm between the present apparatus and the operation field.

Figure 4A:
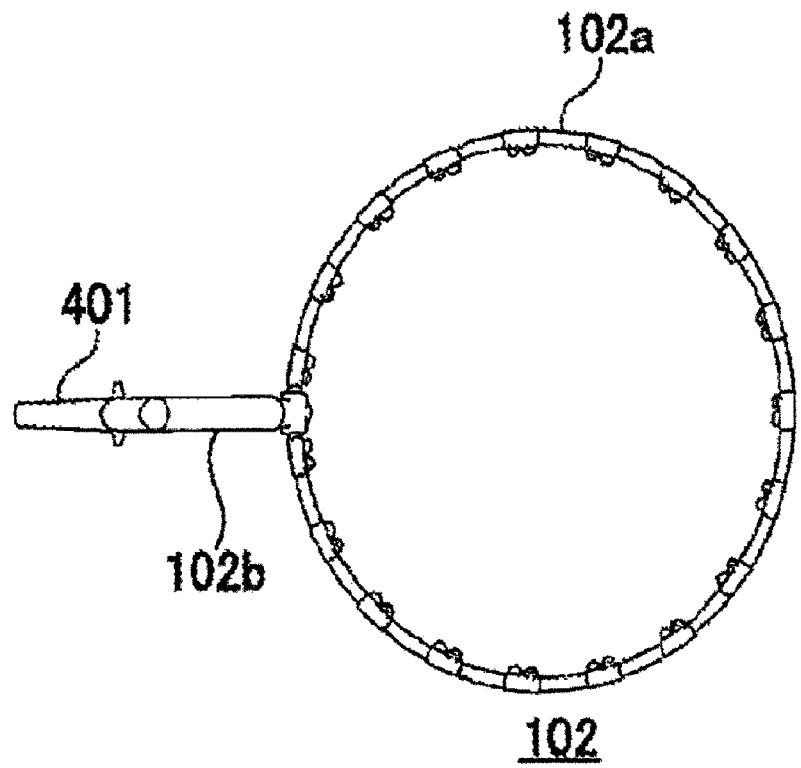
FIGS. 4A-4F is six diagrams illustrating the hollow ring type multi-viewpoint video capturing device.
Figure 4B:
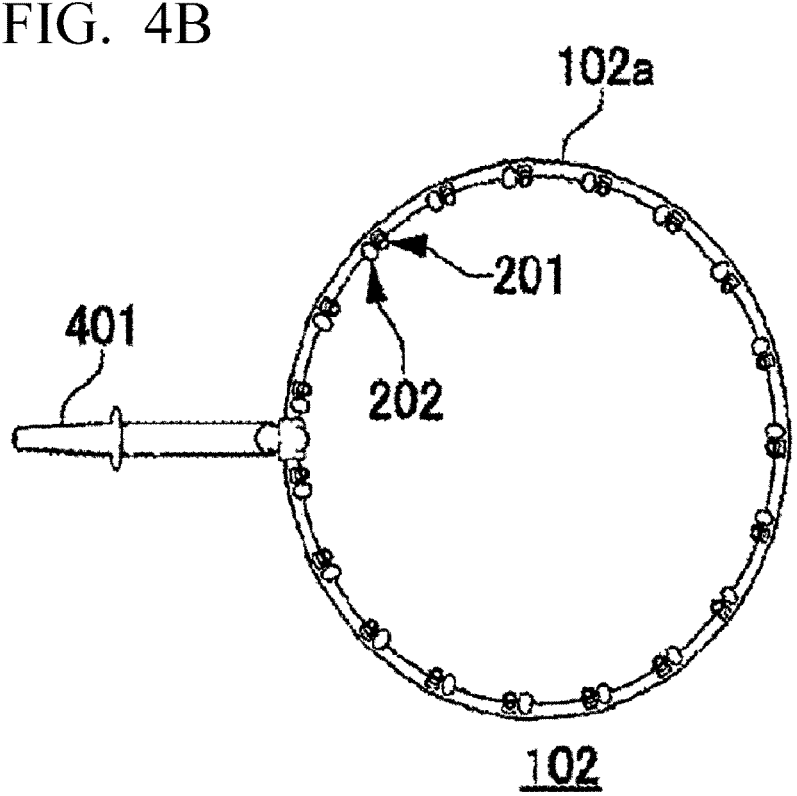
Figure 4C:
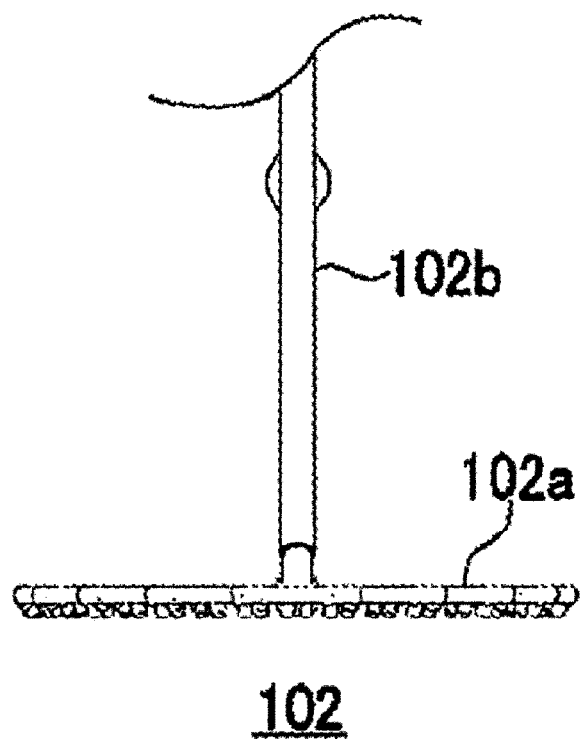
Figure 4D:
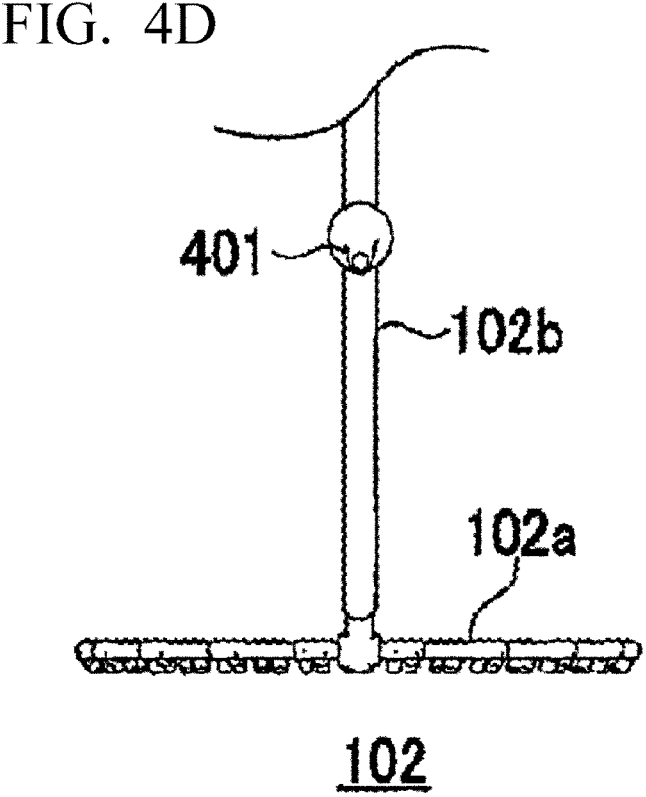
Figure 4E:
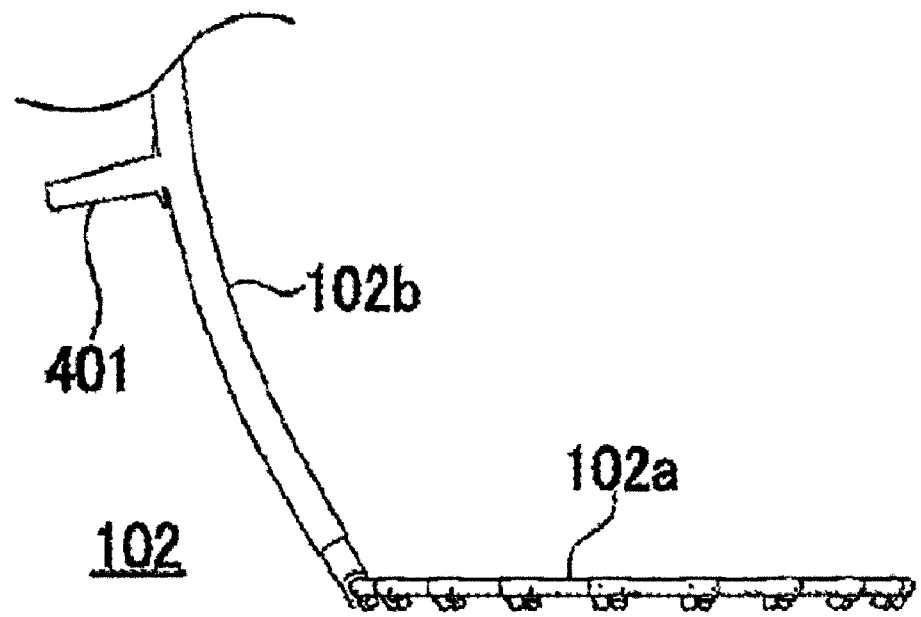
Figure 4F:
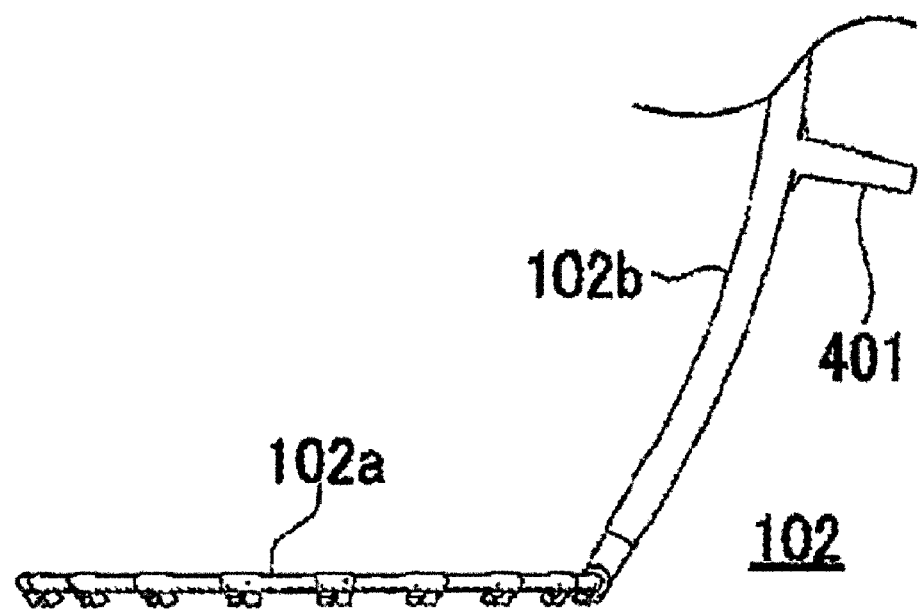

FIG. 4A is a top view of the imaging lighting instrument 102, FIG. 4B is a bottom view of the imaging lighting instrument 102, FIG. 4C is a front view of the imaging lighting instrument 102, FIG. 4D is a rear view of the imaging lighting instrument 102, and FIGS. 4E and 4F are side views of the imaging lighting instrument 102.

As is apparent from FIGS. 4A, 4B, 4D, 4E and 4F, the fixing instrument 102b is provided with a handle 401 for the surgeon 107 to dispose the imaging lighting instrument 102 at an appropriate position.

Figure 5:
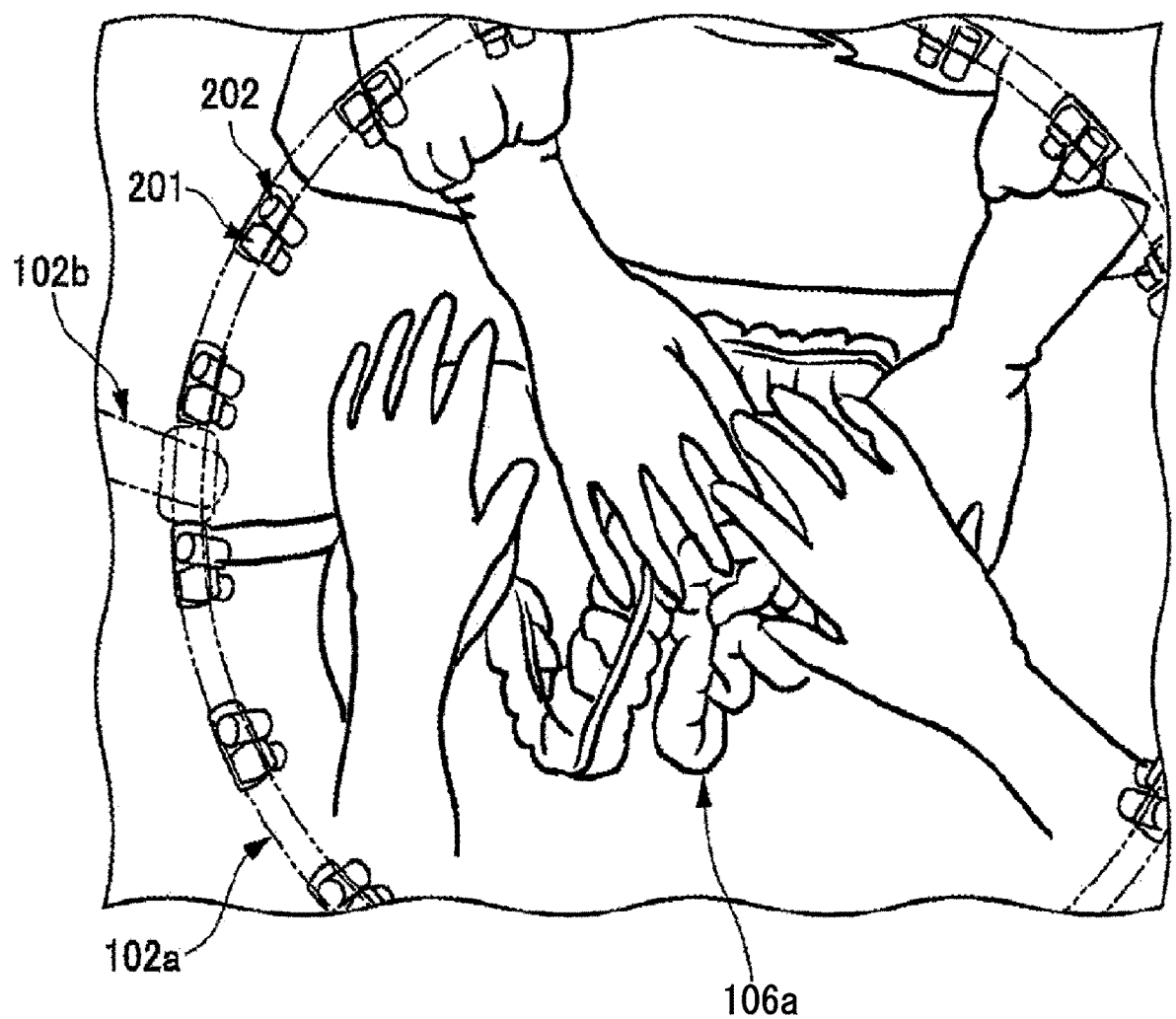
FIG. 5 is a simulation diagram viewed from a surgeon's viewpoint when the hollow ring type multi-viewpoint video capturing device is used.

FIG. 5 is a diagram illustrating a simulation of the operation field when viewed from the viewpoint of the surgeon 107. Although the present device is partially visible on the edge of the field of vision, operation work can be performed comfortably enough because there are few parts blocking the operation field.

FIGS. 6, 7 and 8 illustrate modification mode examples of various shapes of the present device.

Figure 6A:
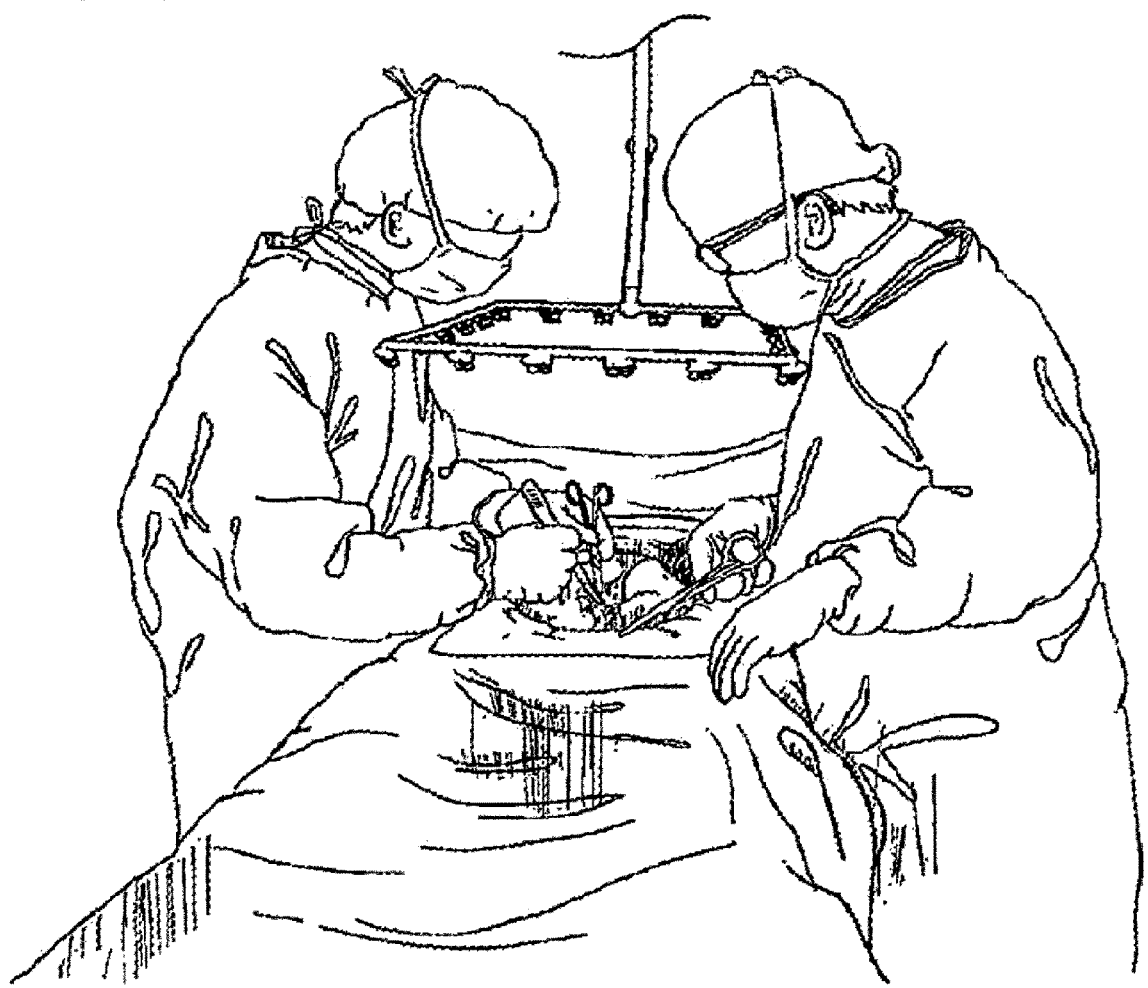
FIGS. 6A-6D is a diagram illustrating an example of a variation in installation (a polygonal shape, an arc shape) of the multi-viewpoint video capturing device.
Figure 6B:
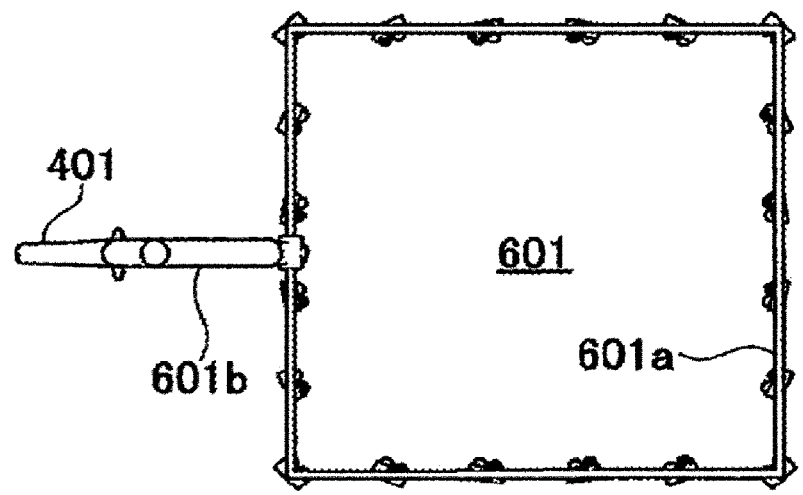

FIG. 6A is a simulation diagram in an operating room using an imaging lighting instrument 601 according to a modification mode example of a first shape, and FIG. 6B is a top view of the imaging lighting instrument 601 according to the modification mode example of the first shape.

The imaging lighting instrument 601 includes a housing 601a having a rectangular shape and a fixing instrument 601b. The fixing instrument 601b is provided with a handle 401 in the same manner as the imaging lighting instrument 102 described above.

Figure 6C:
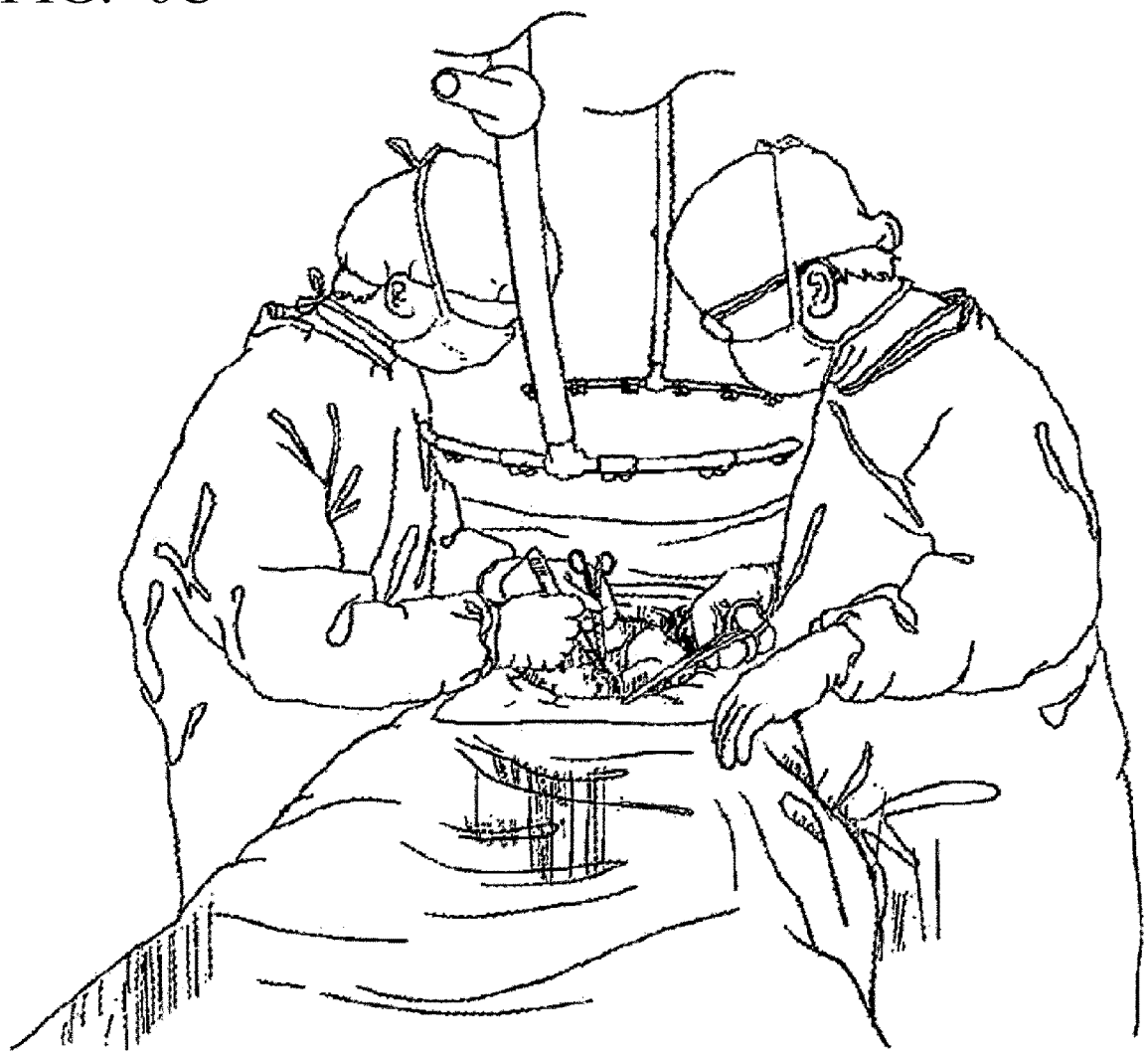
Figure 6D:
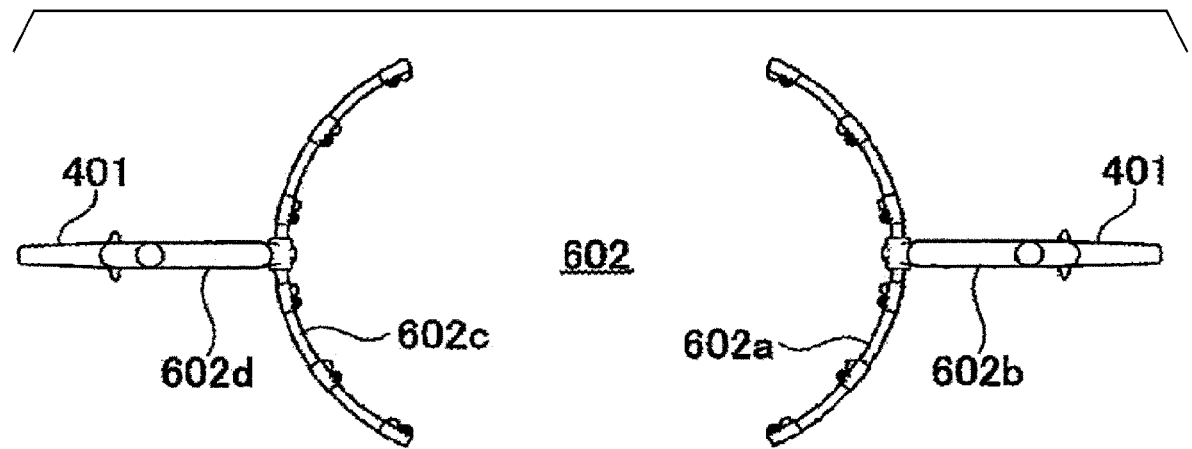

FIG. 6C is a simulation diagram in an operating room using an imaging lighting instrument 602 according to a modification mode example of a second shape, and FIG. 6D is a top view of the imaging lighting instrument 602 according to the modification mode example of the second shape.

The imaging lighting instrument 602 includes a first housing 602a having an arc shape, a first fixing instrument 602b, a second housing 602c having an arc shape, and a second fixing instrument 602d. Each of the first fixing instrument 602b and the second fixing instrument 602d is provided with a handle 401 in the same manner as the imaging lighting instrument 102 described above.

Figure 7A:
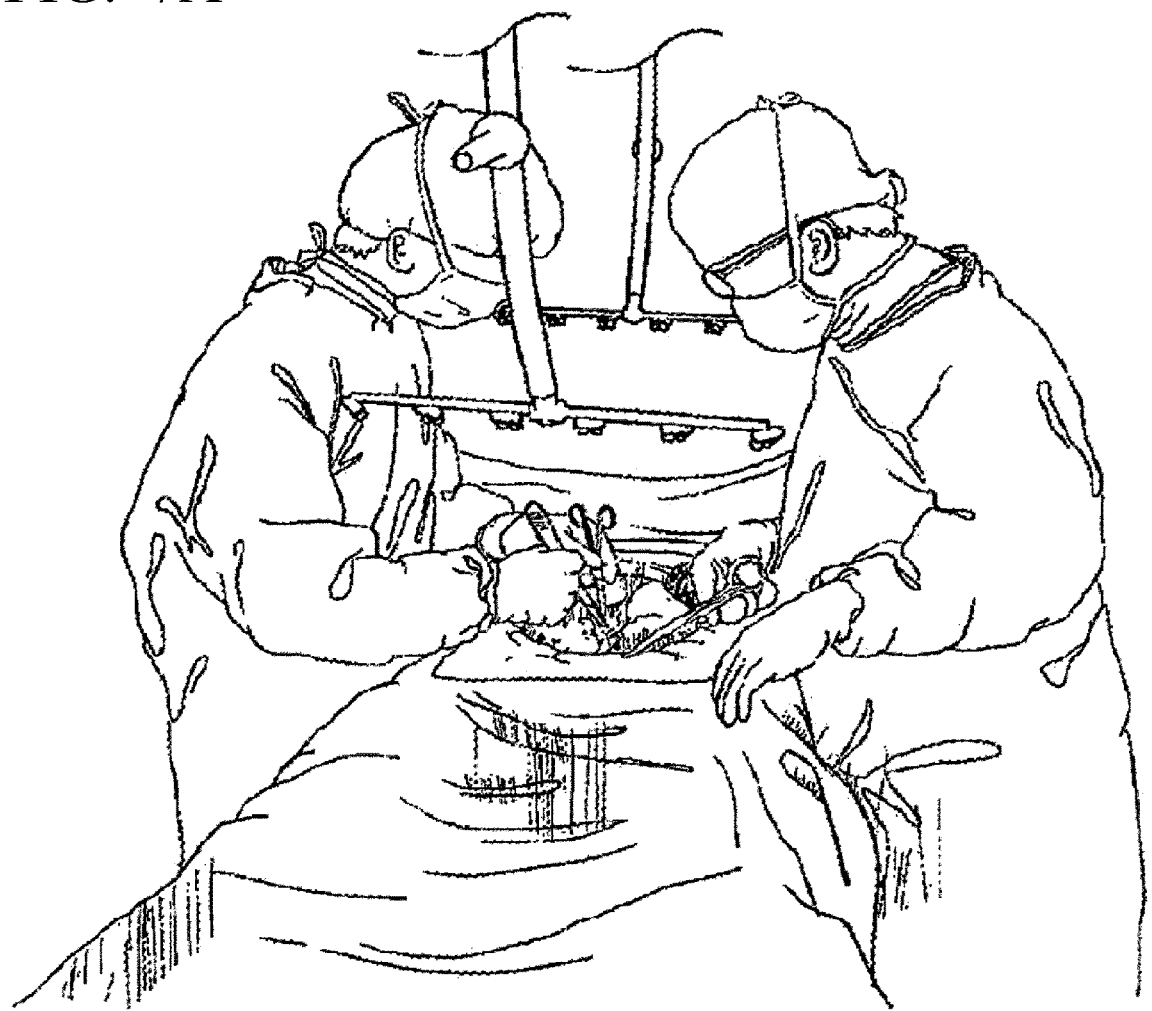
FIGS. 7A-7D) is a diagram illustrating an example of a variation in installation (a linear shape, a V-shape) of the multi-viewpoint video capturing device.
Figure 7B:
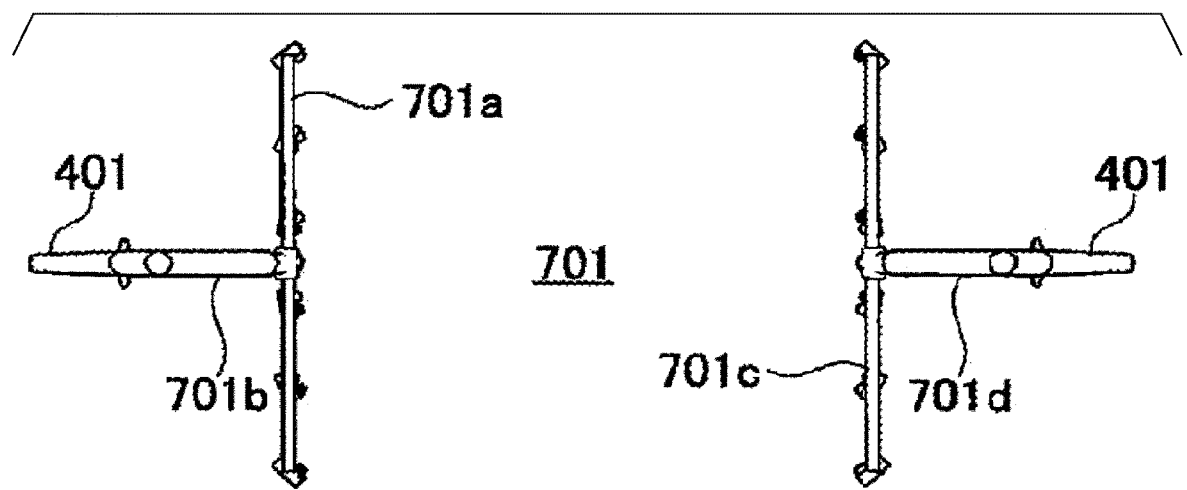

FIG. 7A is a simulation diagram in an operating room using an imaging lighting instrument 701 according to a modification mode example of a third shape, and FIG. 7B is a top view of the imaging lighting instrument 701 according to the modification mode example of the third shape.

The imaging lighting instrument 701 includes a first housing 701a having a linear shape, a first fixing instrument 701b, a second housing 701c having a linear shape, and a second fixing instrument 701d. Each of the first fixing instrument 701b and the second fixing instrument 701d is provided with a handle 401 in the same manner as the imaging lighting instrument 102 described above.

Figure 7C:
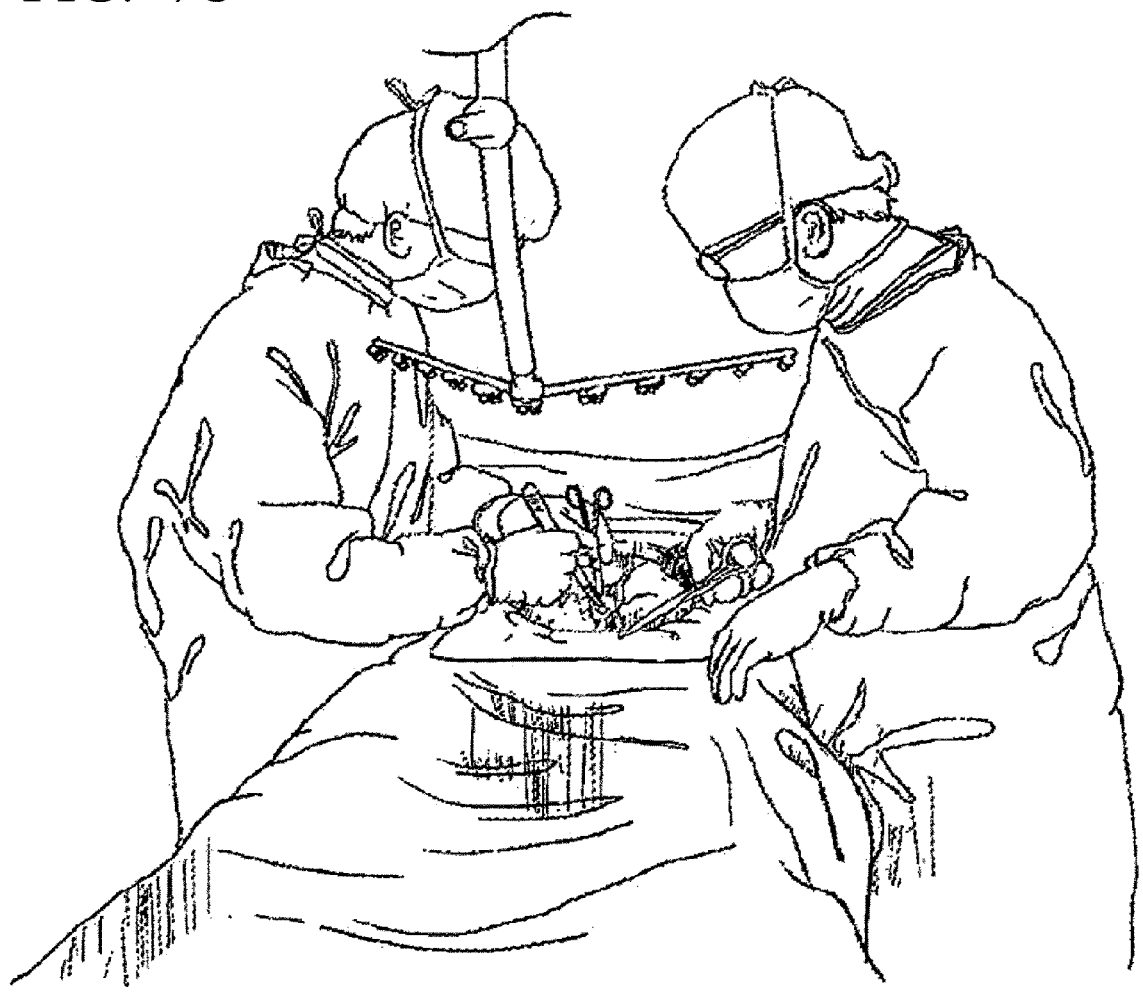
Figure 7D:
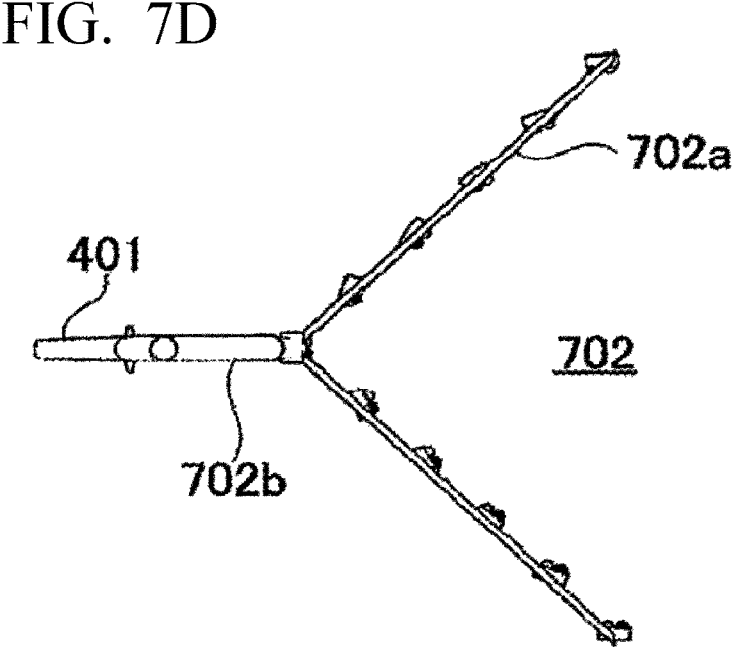

FIG. 7C is a simulation diagram in an operating room using an imaging lighting instrument 702 according to a modification mode example of a fourth shape, and FIG. 7D is a top view of the imaging lighting instrument 702 according to the modification mode example of the fourth shape.

The imaging lighting instrument 702 includes a housing 702a having a V-shape and a fixing instrument 702b. The fixing instrument 702b is provided with a handle 401 in the same manner as the imaging lighting instrument 102 described above.

Figure 8A:
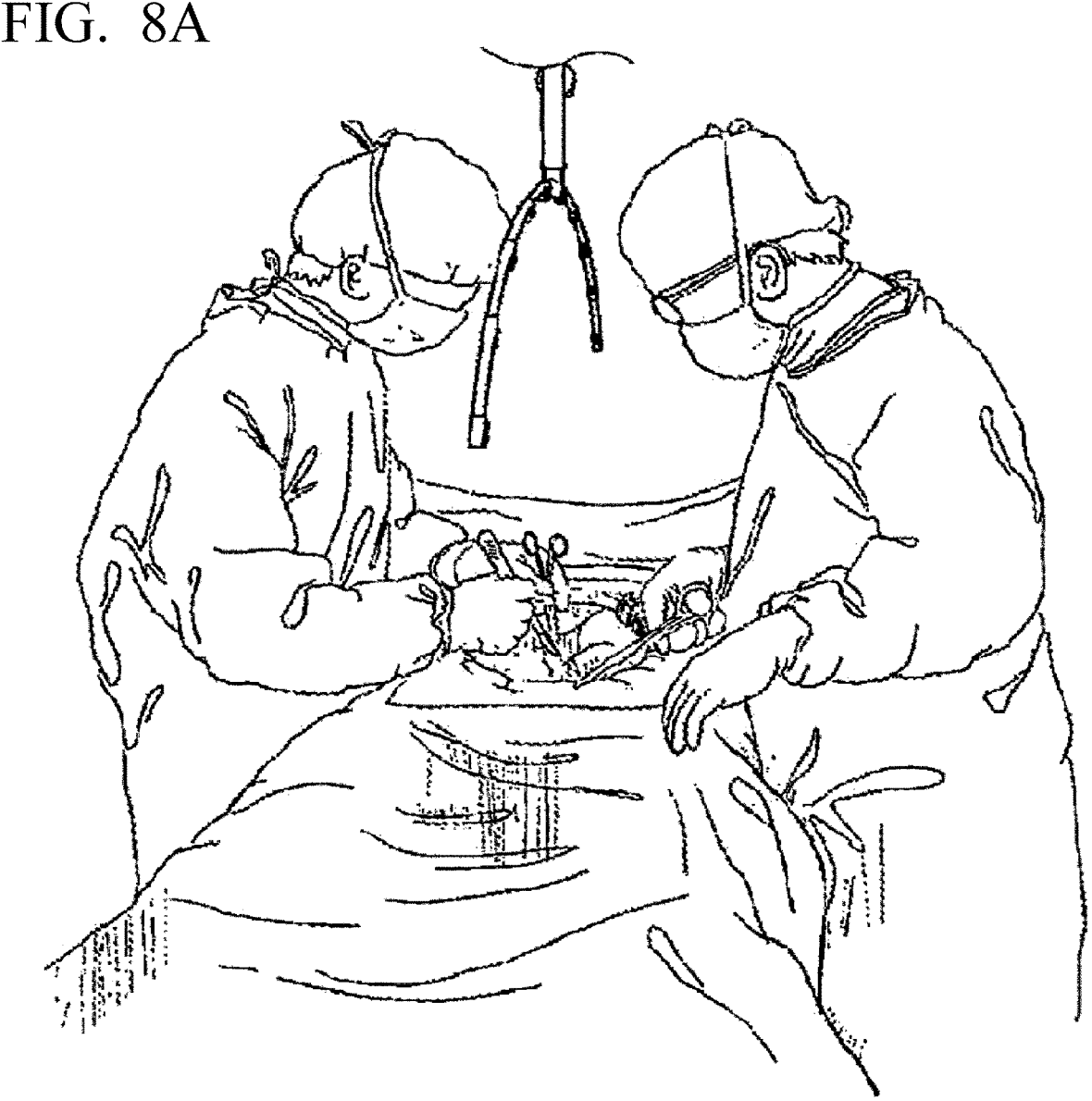
FIGS. 8A-8F is a diagram illustrating an example of a variation in installation (an arch type, a combined type) of the multi-viewpoint video capturing device.
Figure 8B:
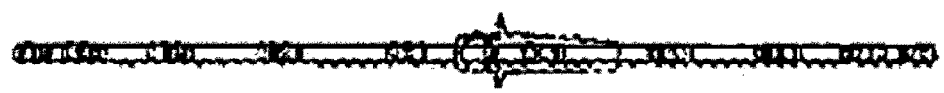
Figure 8C:
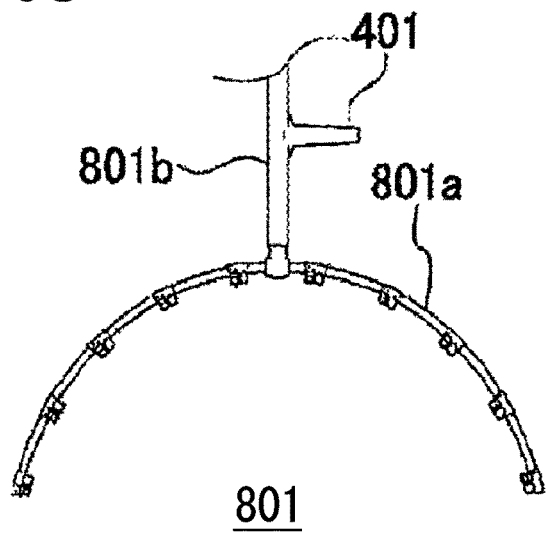

FIG. 8A is a simulation diagram in an operating room using an imaging lighting instrument 801 according to a modification mode example of a fifth shape, FIG. 8B is a top view of the imaging lighting instrument 801 according to the modification mode example of the fifth shape, and FIG. 8C is a diagram illustrating the imaging lighting instrument 801 according to the modification mode example of the fifth shape when viewed in the horizontal direction.

The imaging lighting instrument 801 includes a housing 801a having an arc shape in the vertical direction, and a fixing instrument 801b. The fixing instrument 801b is provided with a handle 401 in the same manner as the imaging lighting instrument 102 described above.

Figure 8D:
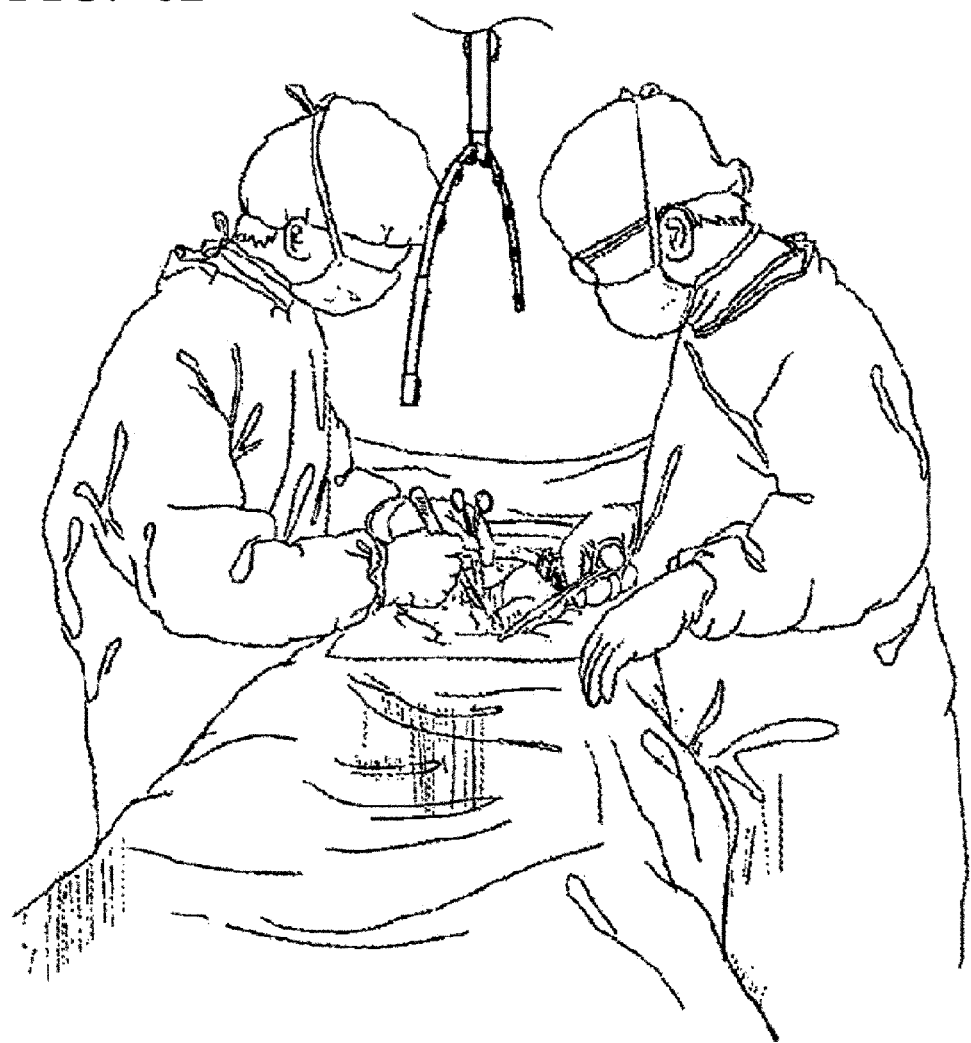
Figure 8E:
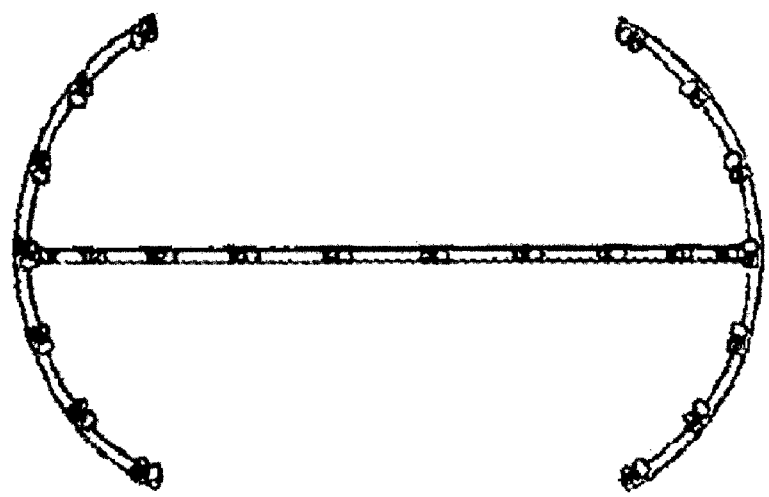
Figure 8F:
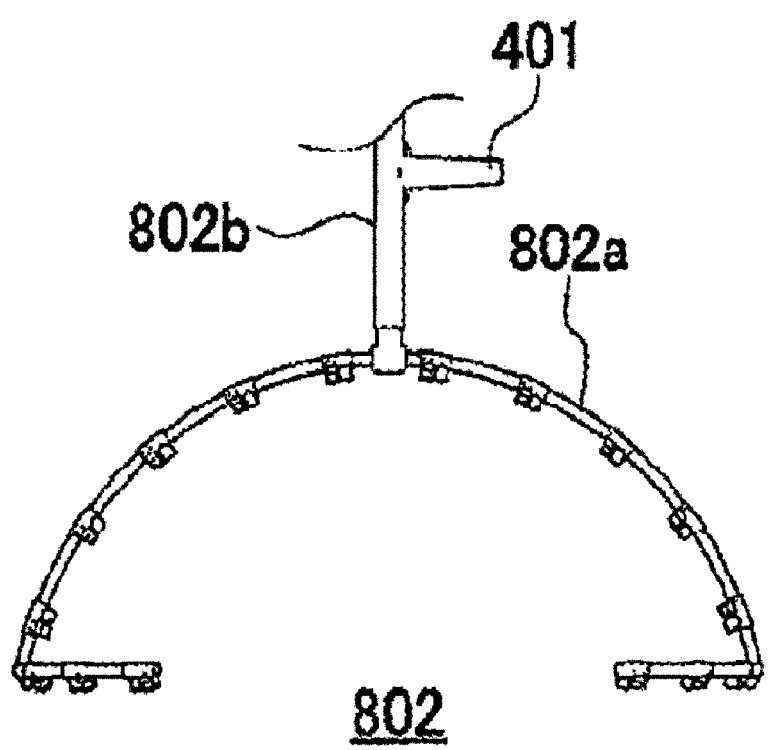

FIG. 8D is a simulation diagram in an operating room using an imaging lighting instrument 802 according to a modification mode example of a sixth shape, FIG. 8E is a top view of the imaging lighting instrument 802 according to the modification mode example of the sixth shape, and FIG. 8F is a diagram illustrating the imaging lighting instrument 802 according to the modification mode example of the sixth shape when viewed in the horizontal direction.

The imaging lighting instrument 802 includes a housing 802a and a fixing instrument 802b, the housing having an arc portion in the vertical direction and further having arc ends at both ends of the arc portion. The fixing instrument 801b is provided with a handle 401 in the same manner as the imaging lighting instrument 102 described above.

Also, in a polygonal shape represented by a square illustrated in FIGS. 6A and 6B, a sufficiently large number of combinations of cameras and lights can be disposed in the same manner as a ring shape which is a basic shape, and thus a multi-viewpoint video can be created.

A C-type×2 in FIGS. 6C and 6D and an I-type×2 in FIGS. 7A and 7B are devised to be able to secure a better field of vision and workability by eliminating a device in front of an operator and an assistant in order to further reduce an obstruction of a field of vision by using a 360-degrees ring type. On the other hand, it is undeniable that the quality of a multi-viewpoint video is likely to deteriorate because the number of cameras and lights that can be disposed is reduced in this format as a compensation for an improvement in a field of vision.

FIGS. 7C and 7D illustrate a V-type device disposed on one side. While the fields of vision and workability of an operator and an assistant are excellent, it is assumed that the quality of a multi-viewpoint video device will deteriorate because the number of combinations of cameras and lights is halved.

On the other hand, FIGS. 8A, 8B, and 8C illustrate modification mode examples in which a plurality of cameras and lights are vertically disposed in an arch shape in a narrow range between an operator and an assistant. It is possible to dispose a large number of cameras and lights in the vertical direction while maintaining the fields of vision and workability of the operator and the assistant.

Modification mode examples in FIGS. 8D, 8E and 8F show a combination of the C-type×2 illustrated in FIG. 6D and the arch type illustrated in FIGS. 8B and 8C. It is possible to maintain good fields of vision and workability of the operator and the assistant and dispose a sufficiently large number of cameras and lights in order to constitute a multi-viewpoint field-of-vision video.

Figure 9A:
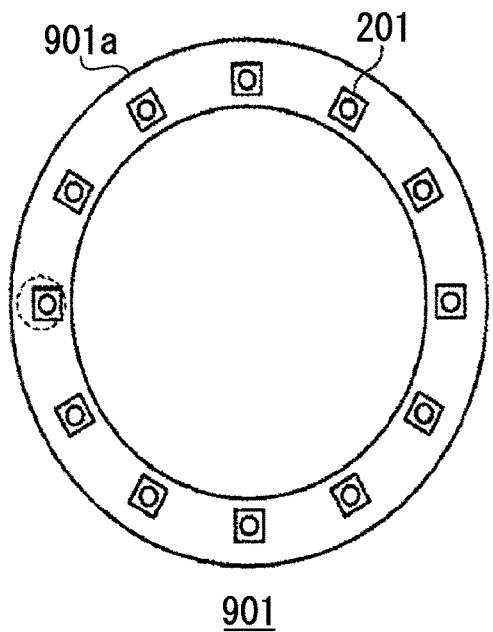
FIGS. 9A-9B is a diagram illustrating an example of a variation having no lighting and installation of an imaging apparatus.
Figure 9B:
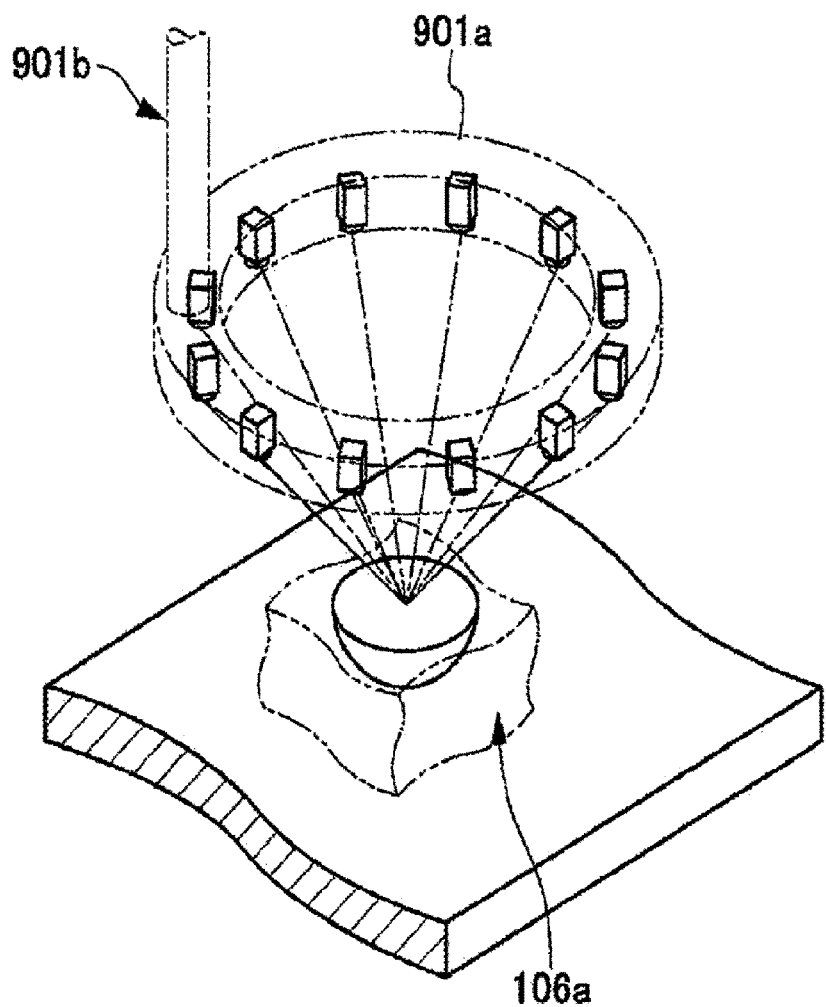

FIG. 9A is a top view of an imaging instrument 901 as a variation having no lighting, and FIG. 9B is a schematic view illustrating the state of use of the imaging instrument 901.

The imaging instrument 901 is configured such that the lights 202 are removed from the imaging lighting instrument 102, and only the plurality of cameras 201 are incorporated into a housing 901a.

The imaging lighting instrument 102 according to the embodiment of the present invention has a basic structure in which both a plurality of cameras and a plurality of lights are alternately disposed. However, as illustrated in FIGS. 9A and 9B, it is also assumed that the imaging lighting instrument 102 is designed and used as the imaging instrument 901 using a plurality of cameras in a variation having no lighting. In this case, a shadowless light installed in an existing operating room can be diverted, and thus it is advantageous in terms of cost when equipment is introduced.

Figure 10A:
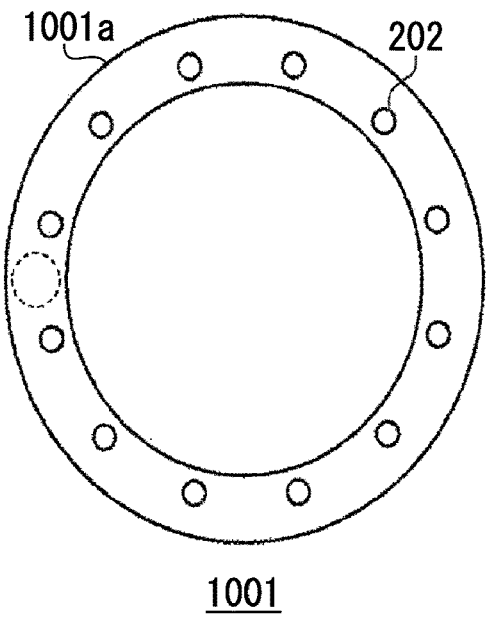
FIGS. 10A-10B is a diagram illustrating an example of a variation having no video capturing device and a lighting apparatus.
Figure 10B:
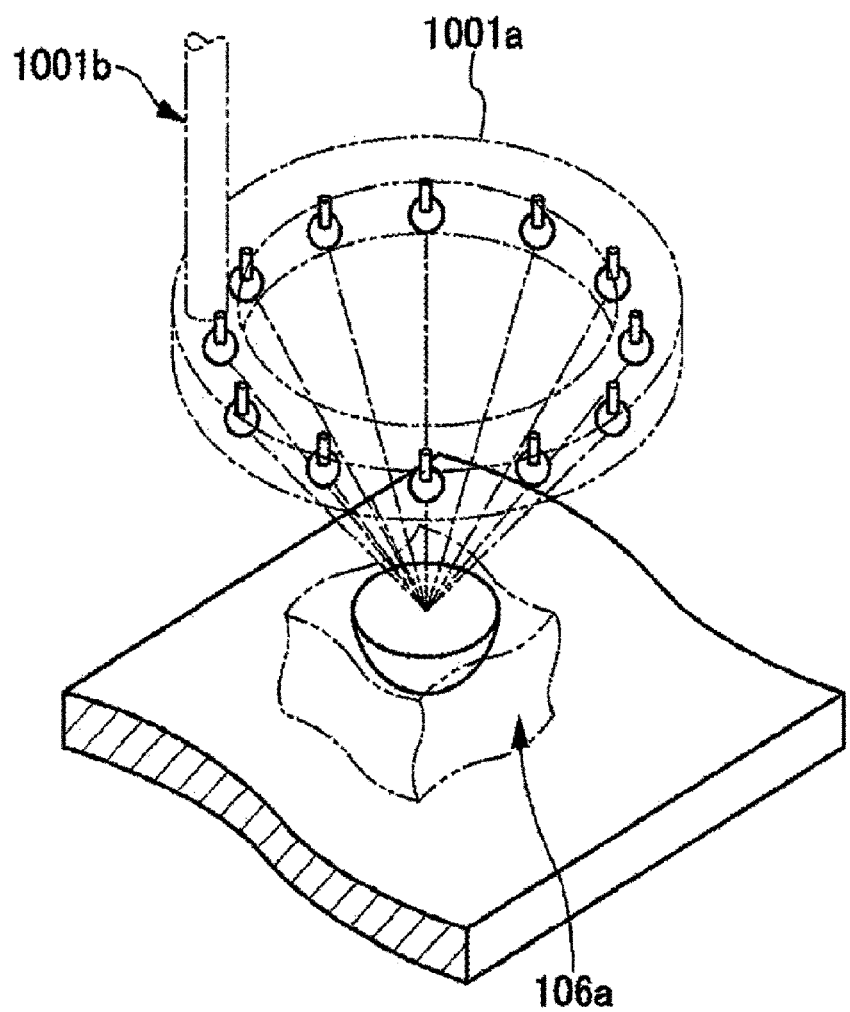

FIG. 10A is a top view of a lighting instrument 1001 as a variation having no camera, and FIG. 10B is a schematic view illustrating the state of use of the lighting instrument 1001.

The lighting instrument 1001 is configured such that the cameras 201 are removed from the imaging lighting instrument 102, and only the plurality of lights 202 are incorporated into a housing 1001a.

The imaging lighting instrument 102 according to the embodiment of the present invention has a basic structure in which both a plurality of cameras and a plurality of lights are, for example, alternately disposed. However, as illustrated in FIGS. 10A and 10B, a variation having only lights is also assumed. In the related art, light from a shadowless lamp installed above the head of the surgeon 107 is blocked by the head or body of the surgeon 107, and it is necessary to frequently adjust the position of the lights. However, the present device installed between the head of a surgeon and a patient is never blocked by the head or body of the surgeon and serves as a completely shadowless lighting device.

The imaging lighting instrument 102 of the present invention is formed in various shapes such as a shape of a straight line having a finite length or a shape of a curve having a finite length as illustrated in FIGS. 3, 4, 5, 6, 7, and 8 in order to minimize the interference with an operator's line of sight. The housing 102a is formed as thin as possible in accordance with the sizes of the plurality of cameras 201 and lights 202 accommodated in the housing 102a. As a result, the thickness of the housing 102a does not interfere with the operator.

Here, the curve is a concept including a straight line in the world of mathematics, and the straight line is a special example of a curve. Thus, it can be said that the imaging lighting instrument 102 in the embodiment of the present invention is formed by a housing made of a wire member of a finite length, including the linear imaging lighting instrument 102. That is, the shape of the imaging lighting instrument 102 of the present invention is not limited to those illustrated in FIGS. 3 4, 5, 6, 7, and 8, and includes all housing shapes for the purpose of not interfering with the field of vision and work of an operator.

The plurality of cameras and the plurality of lights accommodated in the housing made of a wire member of a finite length are all disposed toward the operation field 106a which is a subject.

As described above, the imaging lighting instrument 102 used in the multi-viewpoint video capturing device 101 of the present invention can have various shapes.

The housing 102a is preferably formed of a lightweight and highly rigid material such as an aluminum alloy, polycarbonate, or carbon. However, a configuration in which the cameras 201 and the lights 202 may be attached to a flexible pipe made of stainless steel or the like used in a water pipe or the like so as to be freely deformable in accordance with the form of the operation field 106a may be adopted. The housing can also be deformed into various shapes described above as long as it is a material such as a flexible pipe that can be freely deformed.

Multi-Viewpoint Video Capturing Device 101: Hardware Configuration

Figure 11:
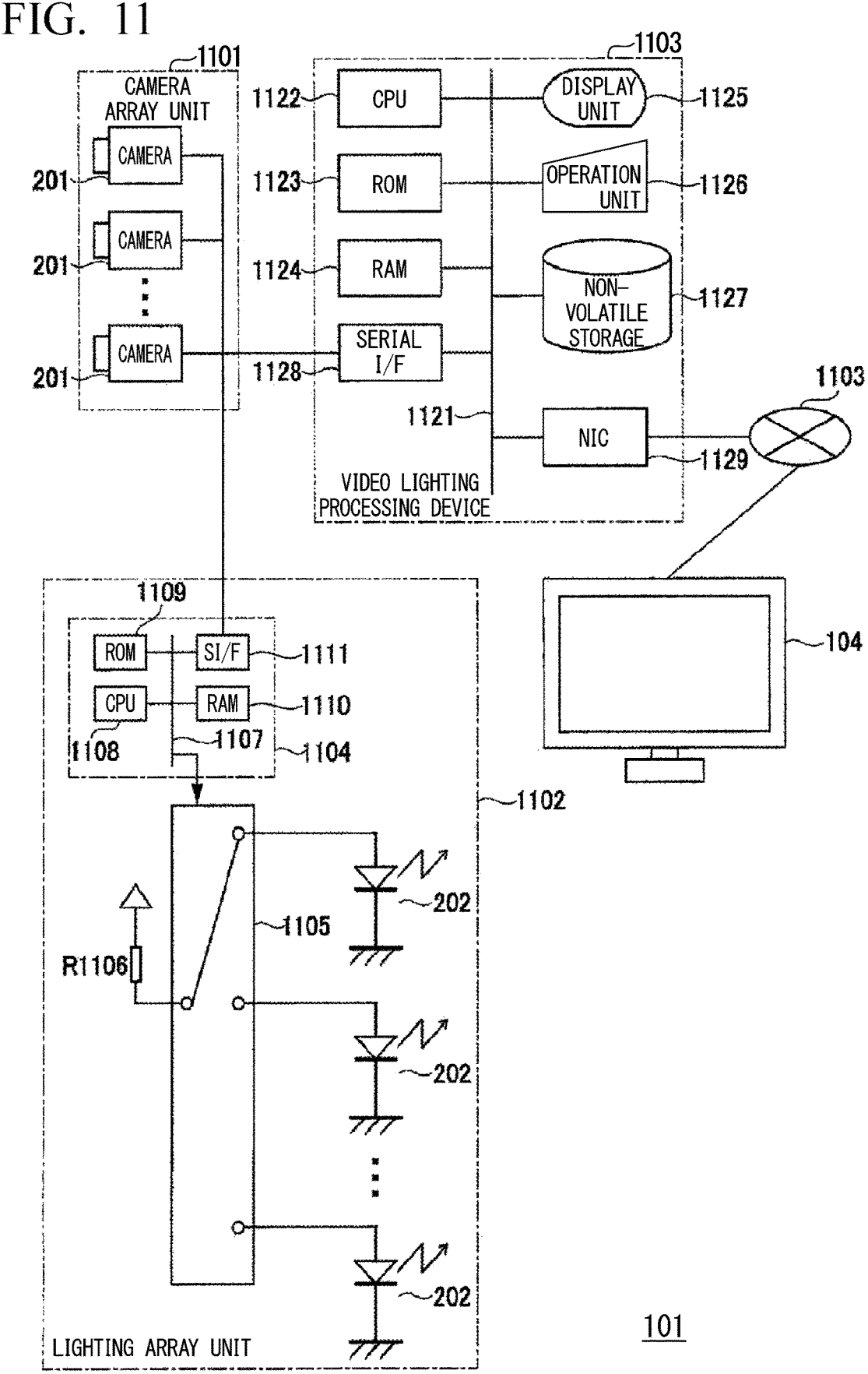
FIG. 11 is a block diagram illustrating a hardware configuration of the multi-viewpoint video capturing device according to the embodiment of the present invention.

FIG. 11 is a block diagram illustrating a hardware configuration of the multi-viewpoint video capturing device 101 according to the embodiment of the present invention.

As illustrated in FIG. 11, the multi-viewpoint video capturing device 101 includes a camera array unit 1101, a lighting array unit 1102, and a video lighting processing device 103 connected thereto.

The camera array unit 1101 and the lighting array unit 1102 are built in the imaging lighting instrument 102.

Further, the large-screen external monitor 104 is connected to the video lighting processing device 103 through a network 1103.

The camera array unit 1101 is an assembly of the plurality of cameras 201 incorporated in the imaging lighting instrument 102 described with reference to FIGS. 1 and 2. The cameras 201 are connected to a serial interface 1128 such as a USB interface included in the video lighting processing device 103.

The lighting array unit 1102 is an assembly of a plurality of lights 202 incorporated in the imaging lighting instrument 102 described with reference to FIGS. 1 and 2. In the lights 202, the emission of the light 202 designated by the video lighting processing device 103 is selectively controlled through a multiplexer 1105 controlled by a microcomputer 1104. In addition, light emission and driving are performed by a current flowing from a power supply voltage node through a current limiting resistor R1106 and the multiplexer 1105. Note that, in the switching control of the multiplexer 1105, it is possible not only to select one light, but also to simultaneously select a plurality of lights including simultaneous turn-on of all of the lights as necessary.

The microcomputer 1104 is connected between the multiplexer 1105 and the video lighting processing device 103, and the microcomputer 1104 controls the multiplexer 1105 in response to a command of the video lighting processing device 103. The microcomputer 1104 is connected to the serial interface 1128 such as a USB interface included in the video lighting processing device 103.

The microcomputer 1104 includes a CPU 1108, a ROM 1109, and a RAM 1110 which are connected to a bus 1107, and a serial interface 1111 (abbreviated as "SI/F" in FIG. 11) such as a USB interface. The multiplexer 1105 is connected to the bus 1107 and controlled by the microcomputer 1104.

The video lighting processing device 103, which is a well-known computer, includes a CPU 1122, a ROM 1123, a RAM 1124, a display unit 1125, an operation unit 1126, and a non-volatile storage 1127 which are connected to a bus 1121.

The CPU 1122 reads a software program for implementing functions of units included in the video lighting processing device 103 from the non-volatile storage 1127 or the ROM 1123 and executes the program.

Videos captured by all of the cameras 201 and received from the camera array unit 1101, variables generated during arithmetic processing performed in video lighting processing device 103, and the like are temporarily written to the RAM 1124. The CPU 1122 executes programs recorded in the non-volatile storage 1127 or the ROM 1123, and thus various functions of the video lighting processing device 103 are implemented.

In addition to the above-described units, the serial interface 1128 such as a USB and a network interface card (NIC) 1129 are connected to the bus 1121 as communication interfaces.

The external monitor 104 is connected to the NIC 1129 through the network 1103. The external monitor 104 includes a well-known computer, and the computer operates a network OS and functions as the external monitor 104 of the video lighting processing device 103.

Although the display unit 1125 of the video lighting processing device 103 may be used as a monitor as it is, there is generally a restriction on the length of a connection cable between the display unit 1125 and the video lighting processing device 103, and thus it is preferable to connect the external monitor 104 through the network 1103.

In addition, when the video lighting processing device 103 is constructed as a network video server, a plurality of external monitors 104 can be easily connected, and thus it is possible to display the same desired video on different monitors at the same time. Thus, even when the external monitor 104 breaks down due to some accident, it is possible to prevent an accident of an operation in advance by operating a preliminary external monitor 104 as it is.

Video Lighting Processing Device 103: Software Function

Figure 12:
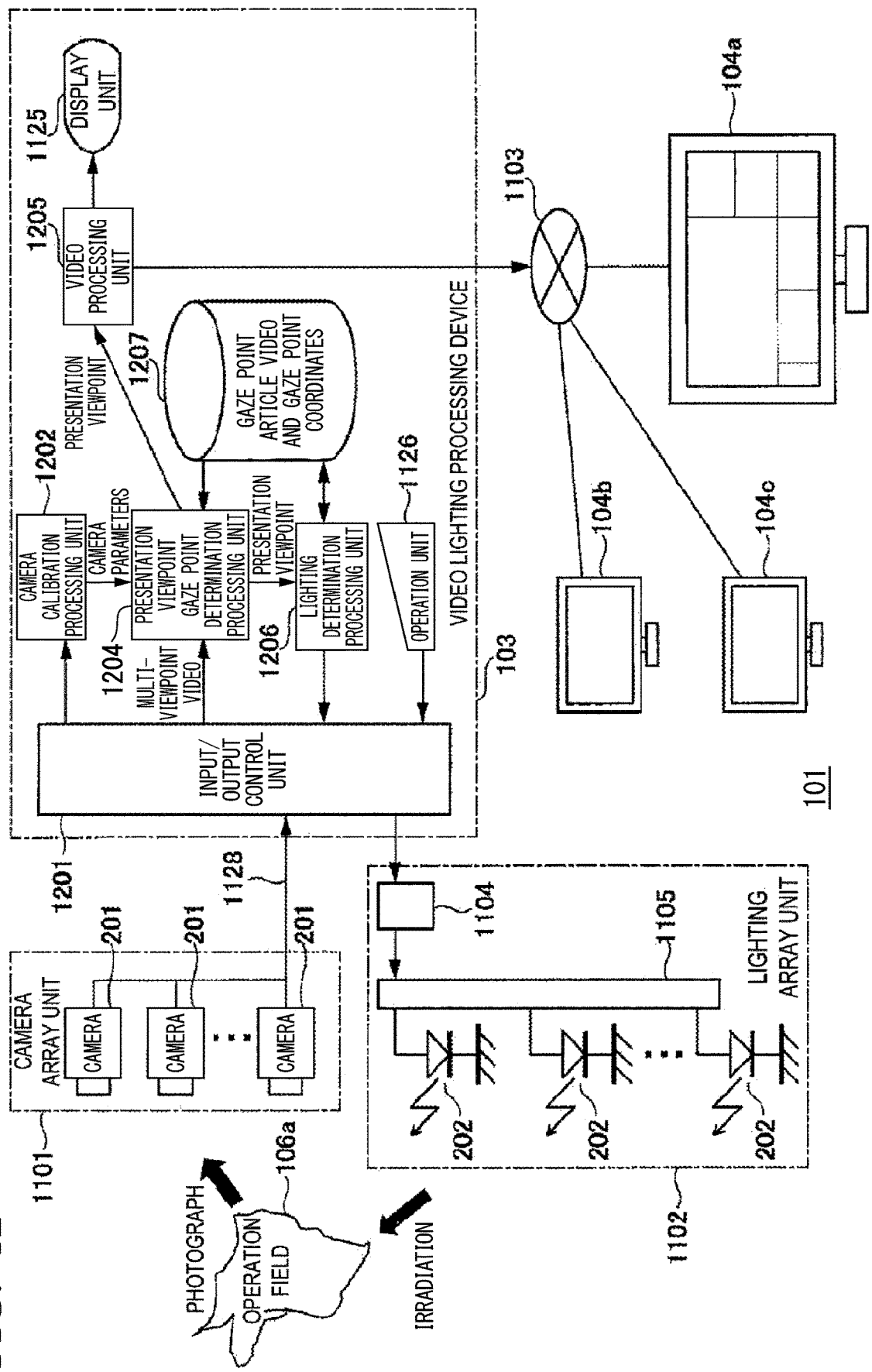
FIG. 12 is a block diagram illustrating a software function of a video lighting processing device.

FIG. 12 is a block diagram illustrating a software function of the video lighting processing device 103.

The video lighting processing device 103 includes an input/output control unit 1201, a camera calibration processing unit 1202, a presentation viewpoint gaze point determination processing unit 1204, a video processing unit 1205, a lighting determination processing unit 1206, and a display unit 1125.

The camera array unit 1101 is constituted by a large number of cameras 1 to N embedded in the imaging lighting instrument 102 and disposed surrounding the periphery of the operation field 106a, and images the operation field 106a from various directions at the time of an operation.

The lighting array unit 1102 is constituted by a large number of LED lights 1 to N usually equal to the number of cameras 201 in the camera array unit 1101, the LED lights being embedded in the imaging lighting instrument 102 together with the cameras 201 and disposed surrounding the periphery of the operation field 106a. In addition, the light emission of the light 202 adjacent to the camera 201 selected by the presentation viewpoint gaze point determination processing unit 1204 is controlled. Further, the light emission of all of the lights is simultaneously controlled as necessary.

The input/output control unit 1201 receives video data obtained from the camera array unit 1101 and also gives control information for switching the lights 1 to N to the lighting array unit 1102.

The input/output control unit 1201 and the camera array unit 1101 are connected by a bidirectional serial interface 1128.

All of the cameras 201 in the camera array unit 1101 transmit video data to the input/output control unit 1201.

The input/output control unit 1201 and the lighting array unit 1102 are connected via a USB interface. When the input/output control unit 1201 receives a turn-on command from the lighting determination processing unit 1206 to be described later, the input/output control unit 1201 transmits a light emission command for the light 202 designated by the lighting determination processing unit 1206 in response to the turn-on command.

The microcomputer 1104 having received the light emission command from the input/output control unit 1201 in the lighting array unit 1102 controls the multiplexer 1105 so as to control the light emission of the designated light 202.

The input/output control unit 1201 and the camera calibration processing unit 1202 are connected by a serial interface. The camera calibration processing unit 1202 estimates camera parameters such as the positions, postures, and focal lengths of the cameras 1 to N constituting the camera array unit 1101 on the basis of video information.

The camera 201 embedded in the imaging lighting instrument 102 is configured with an angle of view at which a common region is observed in videos obtained by the adjacent cameras 201. In addition, camera parameters such as the position, posture, and focal length of each of the cameras 201 with respect to the operation field 106a, which is a subject, are estimated from a correspondence relationship between common observation regions.

In a surgical operation, if an operator is right-handed, for example, the operator often holds a surgical instrument such as an electric scalpel and scissors in the right hand and supports work with forceps or his or her fingers in the left hand to perform operation work. Thus, the location of a subject being a target for work to be noted by the surgeon 107 is within a range of approximately 0 to 5 cm beyond the following two locations.

(1) The tip of a surgical instrument such as a scalpel, forceps, or scissors
(2) The tip of the surgeon's finger that is not holding a surgical instrument Partial image data and a procedure of setting an observation position for each article will be described below.
(1) Case of Surgical Instrument Such as a Scalpel, Forceps, or Scissors A surgical instrument such as a scalpel, forceps, or scissors is imaged by the camera array unit 1101 in advance immediately before an operation, or the like. Video data obtained from the camera array unit 1101 is recorded in the RAM 1124 of the input/output control unit 1201 as multi-viewpoint video data.

Next, a staff member such as a nurse other than the surgeon 107 selects the tip of a surgical instrument such as a scalpel or the like shown in the multi-viewpoint video data using a mouse or the like which is the operation unit 1126. In addition, the staff member such as a nurse also designates two-dimensional coordinates that serve as an observation position on a screen at the time of performing an operation of selecting a surgical instrument such as a scalpel. For example, a range of approximately 0 to 5 cm beyond the tip of a surgical instrument such as a scalpel or forceps is designated as observation position coordinate information.

The partial image data and the observation position coordinate information of surgical instruments such as scalpels, forceps, and scissors, which are extracted from the multi-viewpoint video data, are stored in the RAM 1124 or the non-volatile storage 1127 as a gaze point subject video and gaze point coordinates 1207.
(2) Case of Surgeon's Finger Prior to an operation, an operator performs several shots by the camera array unit 1101 with his or her finger without holding a surgical instrument such as a scalpel. At the time of the imaging, the operator performs imaging while performing various techniques. Video data obtained from the camera array unit 1101 is recorded in the RAM 1124 of the input/output control unit 1201 as multi-viewpoint video data. Next, a staff member such as a nurse other than the surgeon 107 selects the tip of the operator's finger shown in the multi-viewpoint video data using a mouse or the like which is the operation unit 1126. In addition, the staff member such as a nurse also designates two-dimensional coordinates that serve as an observation position on a screen at the time of performing a selection operation by the operator' hand. For example, in a case where the surgeon is right-handed, a range of approximately 0 to 5 cm from the tip of an index finger of the left hand is designated as observation position coordinate information.

The extracted partial image data and the observation position coordinate information of the operator's hand are stored in the RAM 1124 or the non-volatile storage 1127 as the gaze point subject video and the gaze point coordinates 1207.

The reason why a plurality of pieces of multi-viewpoint video data of an operator's finger are prepared is because the finger freely changes the shape thereof, and thus it is necessary to prepare a plurality of pieces of multi-viewpoint video data as the gaze point subject video and the gaze point coordinates 1207 in order to increase the probability of image matching.

Note that the gaze point refers to a three-dimensional point which is estimated by applying triangulation based on camera parameters to a representative point (two-dimensional point) of a partial region of a subject to be noted by the operator in multi-viewpoint image data obtained from the camera array unit 1101.

The input/output control unit 1201 and the presentation viewpoint gaze point determination processing unit 1204 are connected by a serial interface. The presentation viewpoint gaze point determination processing unit 1204 detects the location of a subject that the surgeon 107 desires to view from videos received from the input/output control unit 1201 by all of the cameras 201 with reference to the gaze point subject video and the gaze point coordinates 1207, and estimates two-dimensional position coordinates thereof.

Then, the presentation viewpoint gaze point determination processing unit 1204 further determines a presentation viewpoint which is a viewpoint from which the gaze point can be most appropriately imaged. In the presentation viewpoint determination processing performed by the presentation viewpoint gaze point determination processing unit 1204, the camera 201 that performs imaging from a direction suitable for the observation by the surgeon 107 is selected from among the cameras 1 to N constituting the camera array unit 1101 in consideration of the hand of the surgeon 107 and surgical instruments which are shown in a captured image.

The camera calibration processing unit 1202 and the presentation viewpoint gaze point determination processing unit 1204 are connected via a serial interface. The presentation viewpoint gaze point determination processing unit 1204 calculate the location of a subject that the assistant 107b of the surgeon 107a desires to view, that is, three-dimensional coordinates of a gaze point, on the basis of stereo vision from camera parameters such as the position, posture, and a focal length of the camera 201 which are received from the camera calibration processing unit 1202, and the estimated two-dimensional positional coordinates.

When the three-dimensional coordinate information of the gaze point is determined, the presentation viewpoint gaze point determination processing unit 1204 then specifies the camera 201 that clearly images the gaze point.

The above-described processing is presentation viewpoint determination processing performed by the presentation viewpoint gaze point determination processing unit 1204.

Basically, the lighting determination processing unit 1206 generates information for controlling the turn-on of the lights 202 disposed on both sides of the camera 201 which is specified as being a camera that clearly images a gaze point by the presentation viewpoint gaze point determination processing unit 1204. Note that, in a case where a specific camera 201 is not designated, the turn-on of all of the lights lighting is controlled.

The video processing unit 1205 is an interface for outputting the camera 201 that clearly images a gaze point specified by the presentation viewpoint gaze point determination processing unit 1204 to the display unit 1125, the external monitor 104, or the like. The video processing unit 1205 supplies a multi-viewpoint video to the display unit 1125 provided in the operating room and also provides the multi-viewpoint video to the external monitor 104a via the network 1103.

The external monitor 104a can display videos of the plurality of cameras 201 at the same time. Among them, for example, one camera video that is closest to the line of sight of the surgeon 107a and captures a clear video that is not interfered with by hands of a surgeon and an assistant, and surgical instruments is enlarged and displayed as a main image and can be shared by all participating members. In addition, an external monitor 104b and an external monitor 104c serve as display devices that can present image information other than a direct-view video to an operator. For example, the external monitor 104b presents an image, which is obtained from an angle different from the line of sight of the surgeon 107a, to the surgeon 107a, and the external monitor 104c presents image information other than white light which is captured by near infrared rays.

Note that, although not particularly illustrated in the drawing, in order for a viewer or the surgeon 107 to view a multi-viewpoint video intuitively or with a simple operation, a function of manually selecting the camera 201 using an operation unit may be added to the presentation viewpoint gaze point determination processing unit 1204 and/or the video processing unit 1205.

Flow of Processing of Presentation Viewpoint Gaze Point Determination Processing Unit 1204

Figure 13:
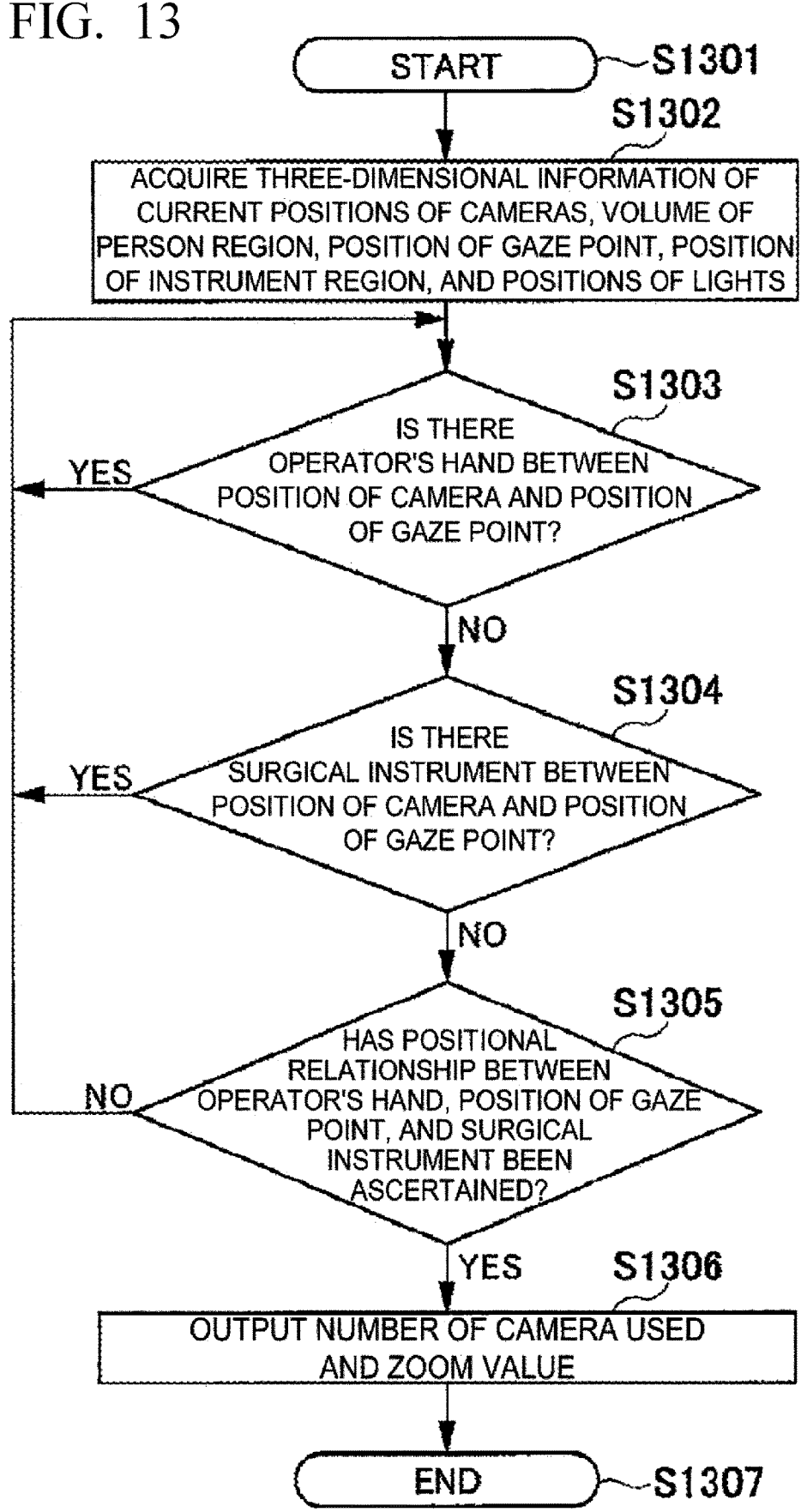
FIG. 13 is a flowchart illustrating a flow of processing of a presentation viewpoint gaze point determination processing unit.

FIG. 13 is a flowchart illustrating a flow of processing of the presentation viewpoint gaze point determination processing unit 1204.

When the processing is started (S1301), the presentation viewpoint gaze point determination processing unit 1204 acquires three-dimensional coordinate information of the positions of the cameras 201, the volume of a person region (mainly the position of the hand of the surgeon 107), the position of a gaze point, and the position of an instrument region, on the basis of a multi-viewpoint video and camera parameters received from the input/output control unit 1201 and the camera calibration processing unit 1202 (S1302).

Next, the presentation viewpoint gaze point determination processing unit 1204 determines whether or not the hand of the surgeon 107 is present between the position of the camera and the position of the gaze point, on the basis of the three-dimensional coordinate information of the gaze point (S1303).

In a case where it is determined in step S1303 that the hand of the surgeon 107 is present between the position of the camera and the position of the gaze point (YES in S1303), a camera in which the hand of the surgeon 107 disappears between the position of the camera and the position of the gaze point is detected.

In a case where it is determined in step S1303 that the hand of the surgeon 107 is not present between the position of the camera and the position of the gaze point (NO in S1303), the presentation viewpoint gaze point determination processing unit 1204 subsequently determines whether or not a surgical instrument is present between the position of the camera and the position of the gaze point, on the basis of the three-dimensional coordinate information of the gaze point (S1304).

In a case where the presentation viewpoint gaze point determination processing unit 1204 determines in step S1304 that a surgical instrument is present between the position of the camera and the position of the gaze point (YES in S1304), a camera in which a surgical instrument is not present between the position of the camera and the position of the gaze point is detected.

In a case where the presentation viewpoint gaze point determination processing unit 1204 determines in step S1304 that a surgical instrument is not present between the position of the camera and the position of the gaze point (NO in S1304), address information of the camera used and a zoom value among the cameras 1 to N are output (S1306), and the series of processes is terminated (S1307).

The above-described multi-viewpoint video capturing device 101 according to the embodiment of the present invention presents live magnification information from a viewpoint different from the naked eye to the surgeon 107 in addition to a direct-view manner with the naked eye, for operations that have been performed so far only in a direct-view manner with the naked eye.

The imaging lighting instrument 102 having the cameras 201 and the lights 202 mounted thereon is positioned between the surgeon 107 and the patient 106, and light of a lighting instrument is not blocked by the heads of the surgeons 107a and 107b, unlike a surgical operation lighting instrument of the related art. Thus, the operation field 106a and the vicinity of the gaze point are always brightly illuminated by the light 202, and the visibility is significantly improved.

Further, the operation field 106a and the vicinity of the gaze point, which are enlarged and displayed by the multi-viewpoint video capturing device 101, are multi-viewpoint videos, and thus it is possible to three-dimensionally confirm the operation field 106a and the vicinity of the gaze point by moving the viewpoint.

In particular, the presentation viewpoint gaze point determination processing unit 1204 specifies three-dimensional coordinate information of a gaze point in a multi-viewpoint video being captured from the three-dimensional coordinate information of the gaze point stored in advance in the gaze point subject video and the gaze point coordinates 1207, and thus switching of an appropriate viewpoint is realized centering on an object to be noted (for example, the tip of a scalpel).

As a result, the object to be noted (for example, the tip of a scalpel) is observed at all times at the same location on the screen, which facilitates observation of the object to be noted.

The multi-viewpoint video capturing device 101 according to the embodiment of the present invention can significantly improve the certainty and safety of an operation in accordance with the above-described features.

Note that, even when the presentation viewpoint gaze point determination processing unit 1204, the lighting determination processing unit 1206, and the gaze point subject video and the gaze point coordinates 1207 are not provided, it is possible to move a presentation viewpoint by a manual operation through the operation unit 1126. However, in this case, since three-dimensional coordinate information of the gaze point is unclear, the viewpoint is switched to center on an object other than the object to be noted (for example, the tip of the scalpel). As a result, the observation position of the object to be noted (for example, the tip of the scalpel) moves on the screen as the viewpoint moves.

First Modification Example: Imaging Lighting Instrument 102 with Ring Directly Placed on Operation Field 106a of Patient 106

Figure 14A:
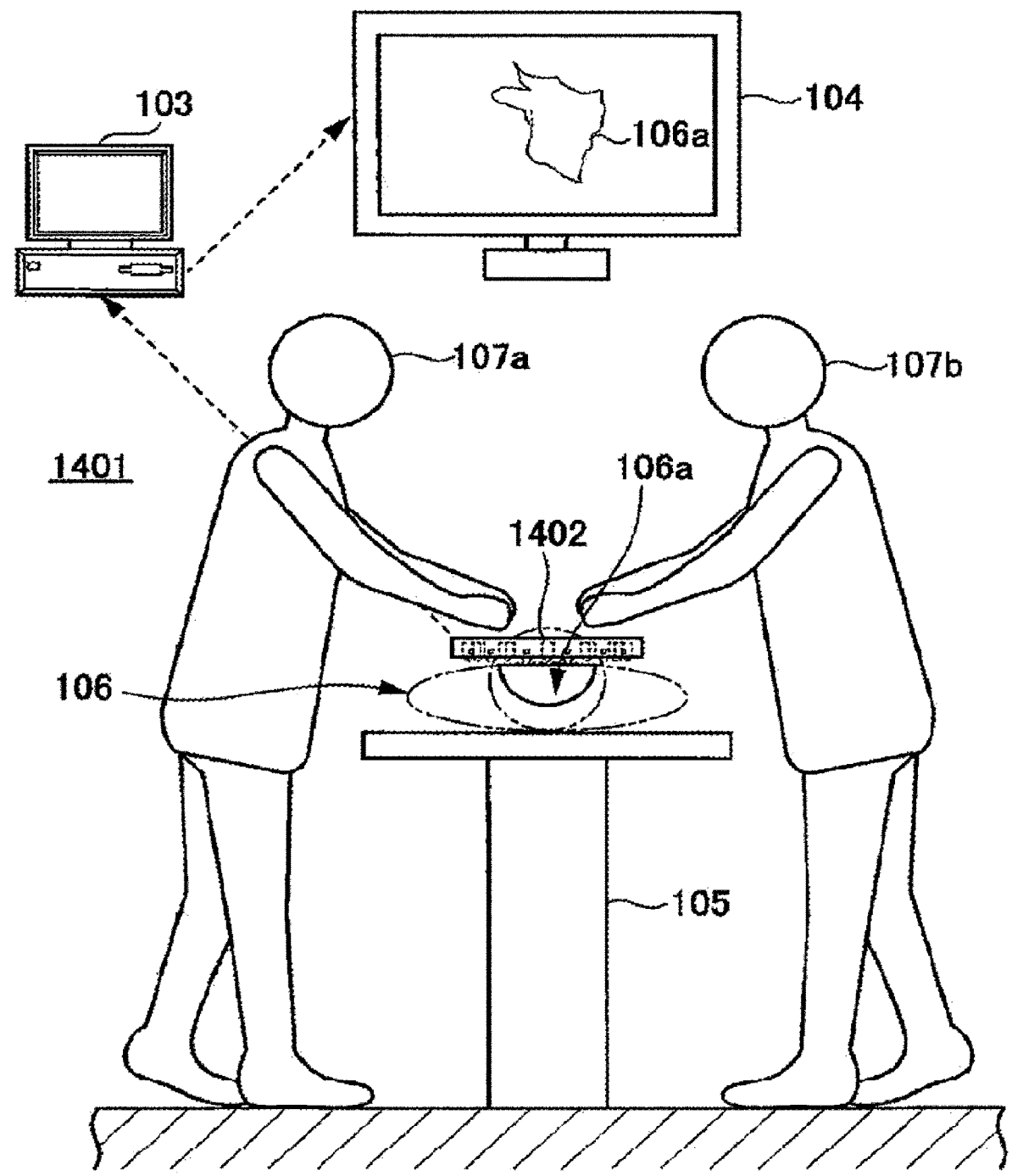
FIGS. 14A-14B is a schematic view illustrating the state of use of a multi-viewpoint video capturing device according to a first modification example of the present invention.
Figure 14B:
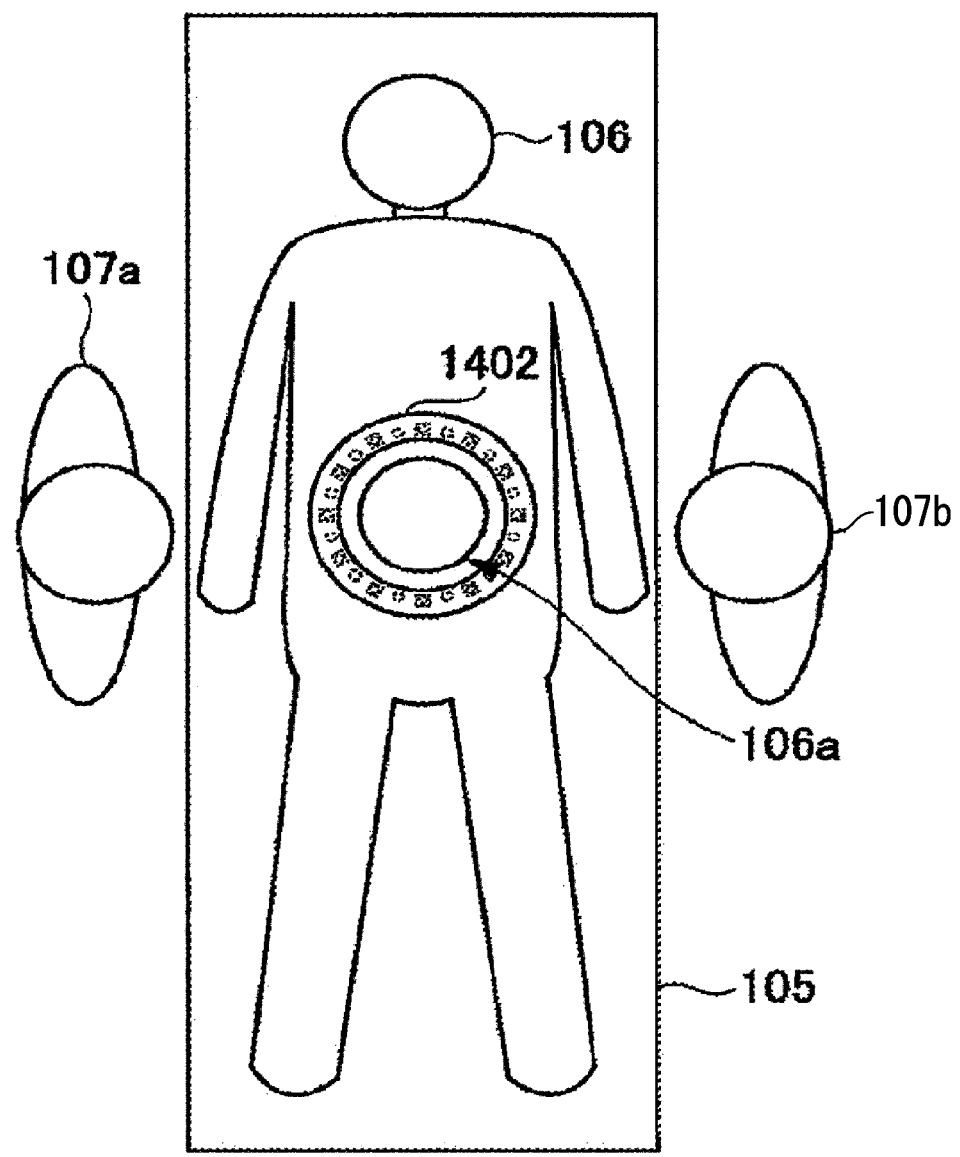

FIG. 14 is a schematic view illustrating the state of use of a multi-viewpoint video capturing device 1401 according to a first modification example of the present invention.

The multi-viewpoint video capturing device 1401 illustrated in FIG. 14 is different from the multi-viewpoint video capturing device 101 illustrated in FIG. 1 in that an imaging lighting instrument 1402 has been miniaturized and placed directly on the operation field 106a of the patient 106.

As described above, in the imaging lighting instrument 102 illustrated in FIG. 1, the hollow ring having the camera array unit 1101 and the lighting array unit 1102 arranged therein is attached to a frame disposed between the patient 106 and the surgeon 107, for example, at a position approximately 30 cm away from the patient 106. Thereby, the surgeon 107 can perform an operation while visually observing the operation field 106a.

Also in the example of FIG. 1, the head of the surgeon 107 an generate a shadow by the lights to eliminate the imperfections of imaging, but the problem is that a frame having the hollow ring attached thereto may interfere with the field of vision of the surgeon 107.

Consequently, in the multi-viewpoint video capturing device 1401 according to the first modification example of the present invention illustrated in FIG. 14, a hollow ring in which the camera array unit 1101 and the lighting array unit 1102 are arranged is installed covering the peripheral edge of the operation field 106a of the patient 106. Also in this case, the surgeon 107 can perform an operation while visually observing the operation field. With this operative method, an operation can be performed in the same state as a normal surgical operation, and thus the surgeon 107 has less hindrance to work as compared with the imaging lighting instrument 102 in FIG. 1. However, since the imaging lighting instrument 1402 comes into contact with the patient 106, there is a possibility that the hands of the surgeons 107a and 107b and surgical instruments will generate shadows by the lights.

Second Modification Example: Imaging Lighting Instrument 102 with Ring Directly Inserted into Operation Field 106a of Patient 106

Figure 15A:
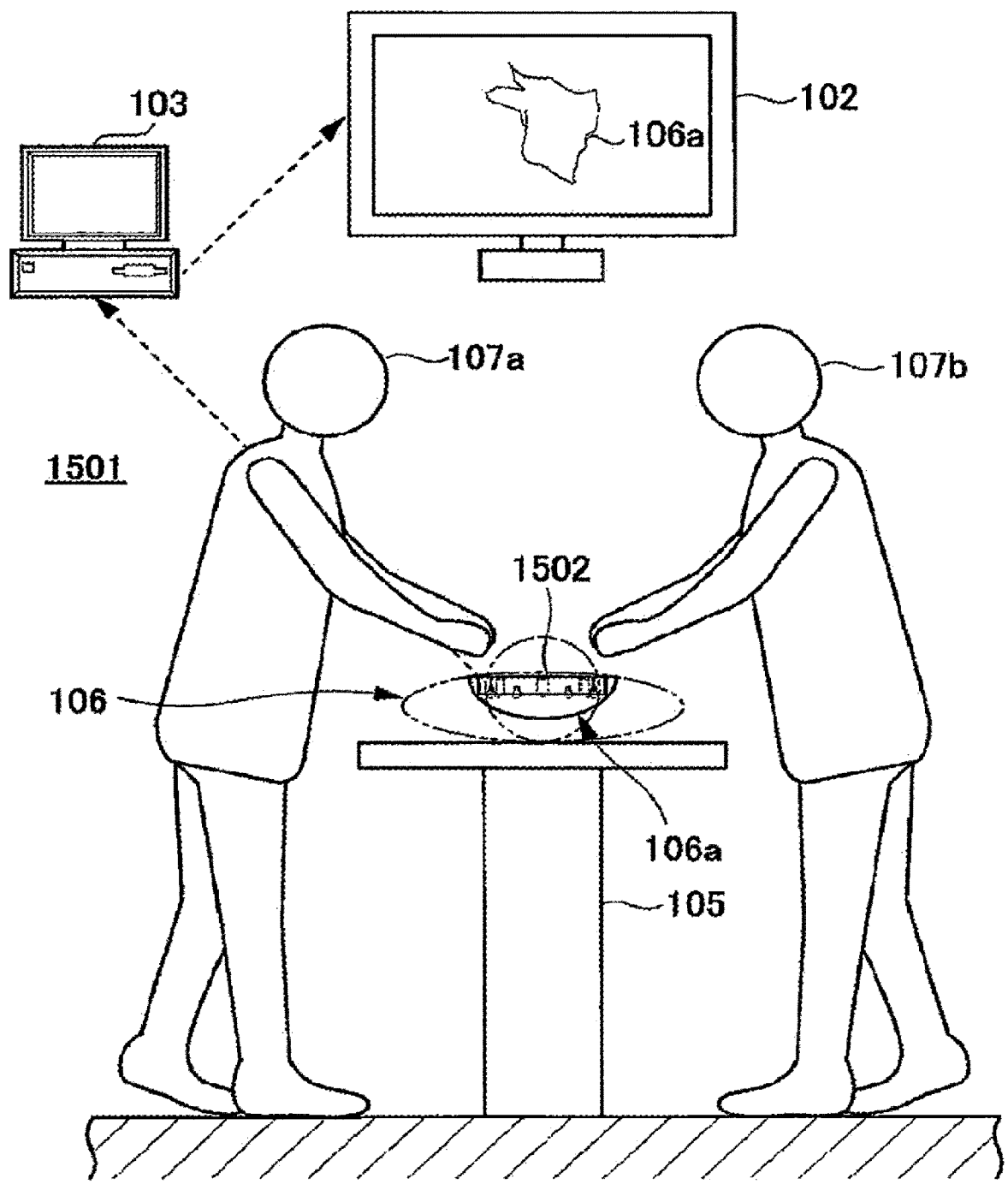
FIGS. 15A-15B is a schematic view illustrating the state of use of a multi-viewpoint video capturing device according to a second modification example of the present invention.
Figure 15B:
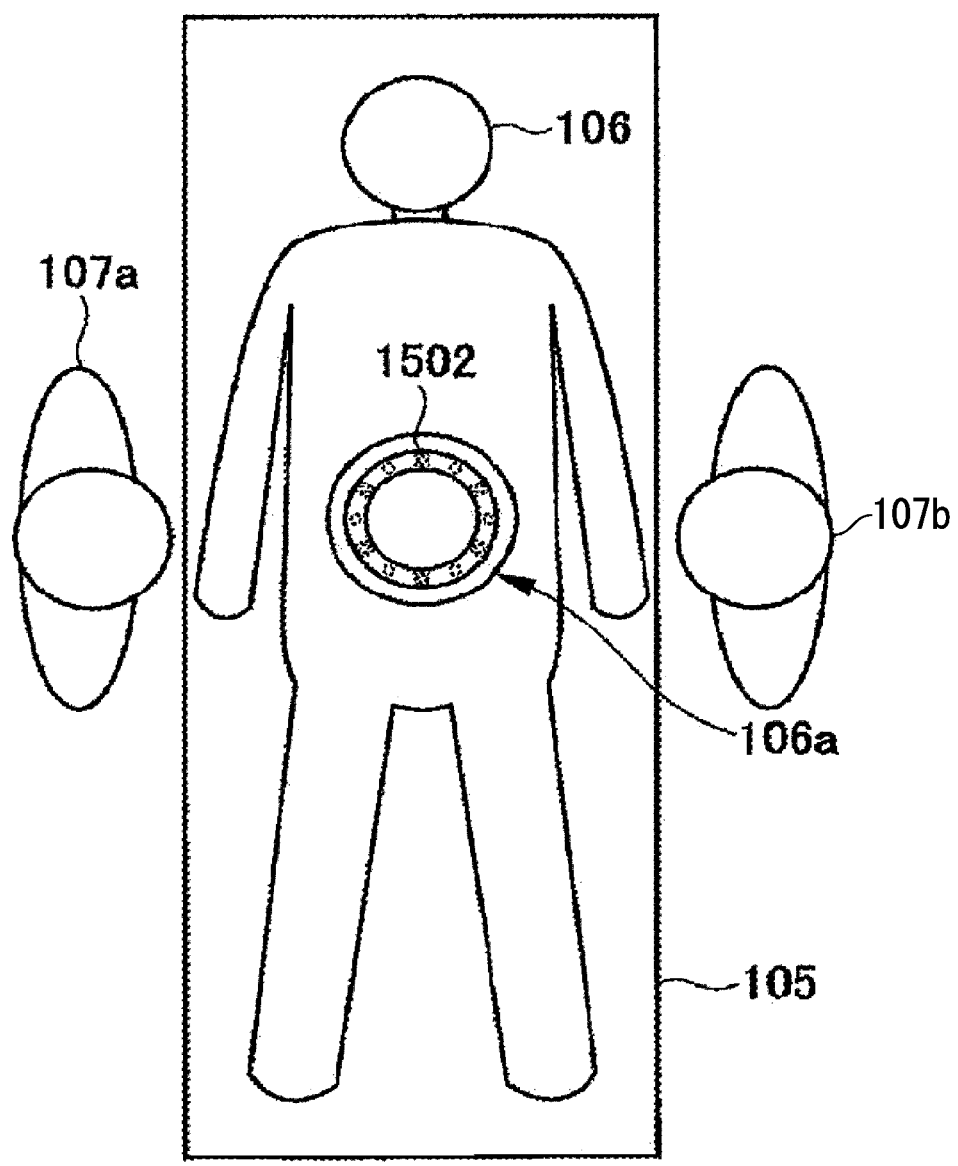

FIG. 15 is a schematic view illustrating the state of use of a multi-viewpoint video capturing device 1501 according to a second modification example of the present invention.

The multi-viewpoint video capturing device 1501 illustrated in FIG. 15 is different from the multi-viewpoint video capturing device 101 illustrated in FIG. 1 and the multi-viewpoint video capturing device 1401 illustrated in FIG. 14 in that an imaging lighting instrument 1502 is smaller than the imaging lighting instrument 1402 according to the first modification example of FIG. 14 and is directly inserted into the operation field 106a of the patient 106.

The imaging lighting instrument 1502 illustrated in FIG. 15 is an example in which a hollow ring in which the camera array unit 1101 and the lighting array unit 1102 are arranged is inserted into the abdominal cavity of the patient 106 and installed to look down on an operation part from above the abdominal cavity. According to this operative method, the surgeons 107a and 107b can perform an operation while viewing a captured video, and the cameras 201 can image the inside of the abdominal cavity without omission.

However, the hollow ring in which the cameras 201 and the lighting array unit 1102 are disposed has to be inserted into and removed from an insertion port provided in the abdomen of the patient 106.

For example, the camera array unit 1101 and the lighting array unit 1102, which are arranged in a line and form a string shape, need to be inserted into the abdominal cavity through the port and deformed into a circle in the abdominal cavity. In addition, after the operation after the imaging is terminated, a mechanism for deforming the camera array unit 1101 and the lighting array unit 1102 into a string shape again and extracting them through the port is required.

Third Modification Example: Imaging Lighting Instrument 1601 for Simultaneously Imaging Blood Vessels in Operation Field 106a of Patient 106 Using Infrared LED 1605 and Cold Mirror 1606 or Hot Mirror When a video of blood vessels is displayed on the external monitor 104 together with a visible light video during a surgical operation, it is possible to prevent the occurrence of a medical accident that damages blood vessels and expect a further improvement in safety.

Figure 16:
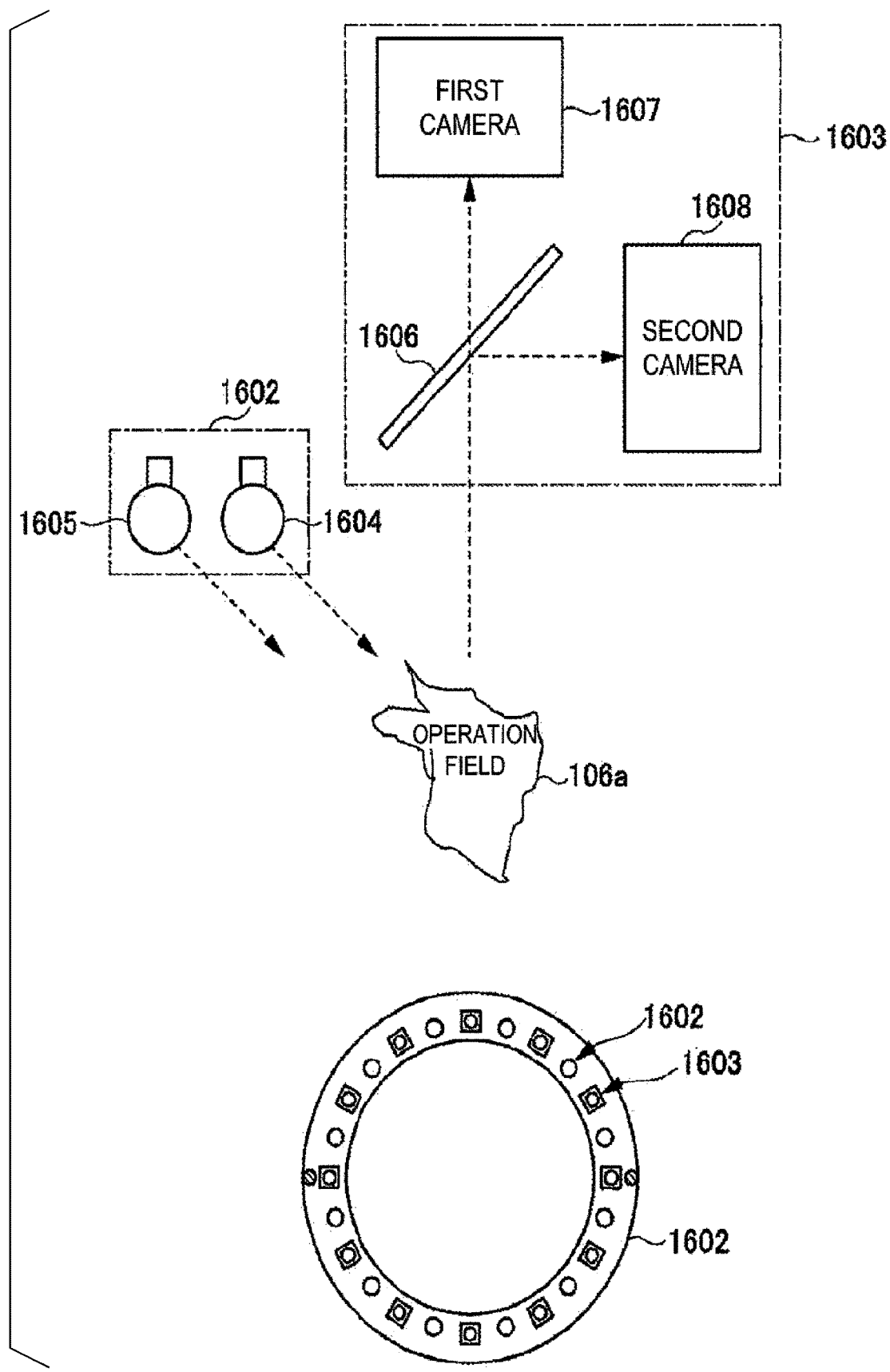
FIG. 16 is a schematic view illustrating an LED light and a camera of an imaging lighting instrument according to a third modification example of the present invention.

FIG. 16 is a schematic view illustrating an imaging lighting instrument 1601 according to a third modification example of the present invention, and an LED light 1602 and a camera unit 1603 which are incorporated in the imaging lighting instrument 1601.

The LED light 1602 includes a visible LED 1604 and an infrared LED 1605. The visible LED 1604 and the infrared LED 1605 continuously emit light at the same time.

The camera unit 1603 includes a cold mirror 1606 obliquely installed at an angle of 45 degrees on the optical axis, a first camera 1007 installed at a position passing through the cold mirror 1606 on the optical axis, and a second camera 1008 installed at a position orthogonal to the cold mirror 1606 on the optical axis.

The cold mirror 1606 transmits near-infrared light and reflects visible light. Thus, the first camera 1007 captures an infrared video, and the second camera 1008 captures a visible light video.

In a case where a hot mirror that transmits visible light and reflects near-infrared light is installed instead of the cold mirror 1606, the first camera 1007 can capture a visible light video, and the second camera 1008 can capture an infrared video.

In either case, a visible light video and an infrared video can be captured simultaneously from incident light, and thus it is possible to display the visible light video and the infrared video on the display unit 1125 and the external monitor 104 at the same time.

Fourth Modification Example: Multi-Viewpoint Video Capturing Device that Images Blood Vessels in Operation Field 106*a* of Patient 106 in Time Division Manner Using Infrared LED 1605

In the third modification example described above, the camera unit 1603 needs to include the cold mirror 1606 or the hot mirror and two cameras 201 therein. There are not many such special products on the market, and it is expensive to make them from ready-made products. However, at the expense of time resolution, it is possible to capture a visible light video and an infrared video at substantially the same time without using a camera having such a special structure.

Figure 17A:
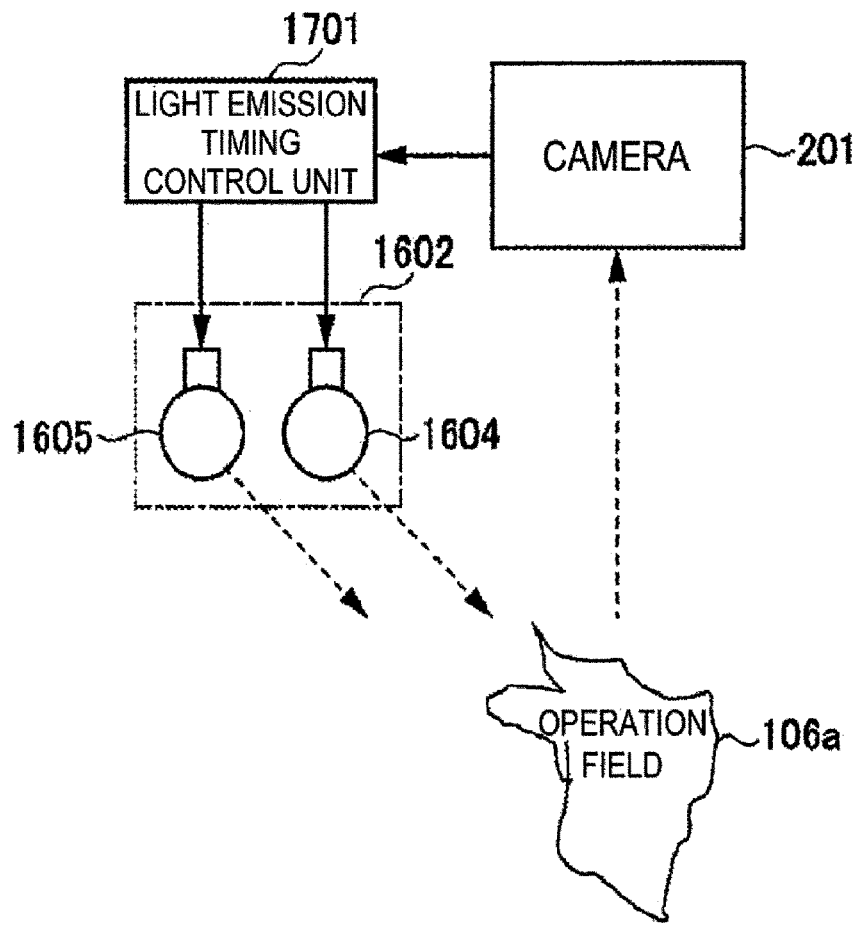
FIGS. 17A-17C is a schematic view illustrating an LED light and a camera of an imaging lighting instrument, is a time chart illustrating light emission timings of a visible LED and an infrared LED, and is a block diagram illustrating a software function of an infrared video acquisition unit provided in an input/output control unit of a video lighting processing device according to a fourth modification example of the present invention.
Figure 17B:
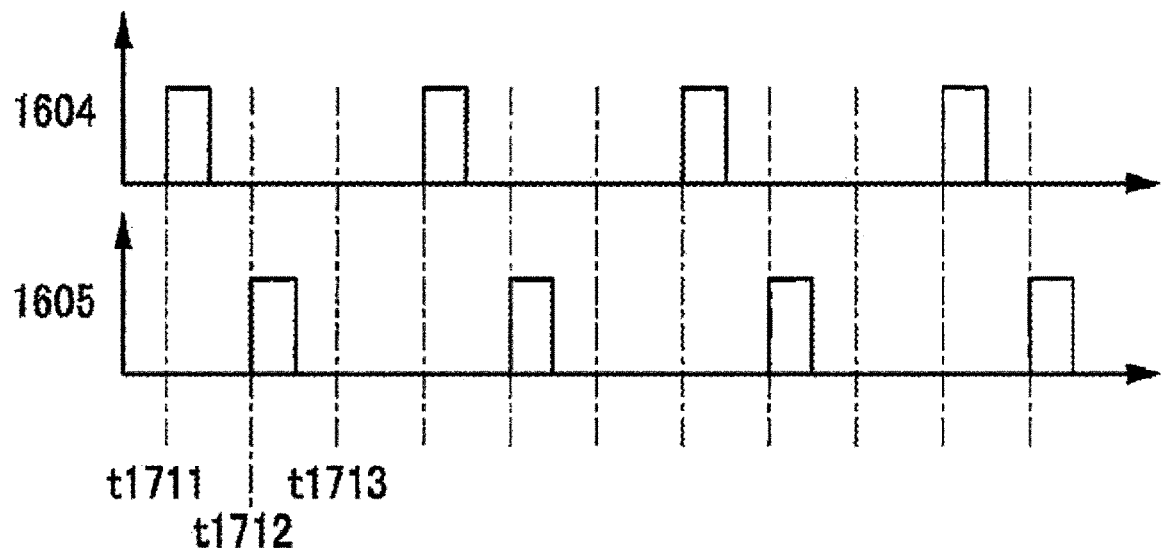
Figure 17C:
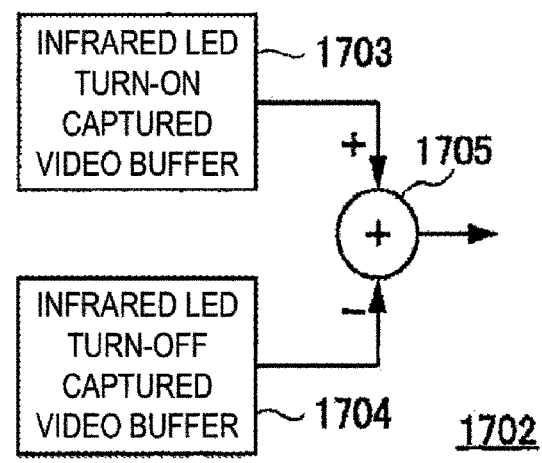

FIG. 17A is a schematic view illustrating the LED light 1602 and the camera 201 of the imaging lighting instrument according to a fourth modification example of the present invention, and FIG. 17B is a time chart illustrating light emission timings of the visible LED 1604 and the infrared LED 1605. In addition, FIG. 17C is a block diagram illustrating software functions of an infrared video acquisition unit 1702 provided in the input/output control unit 1201 of the video lighting processing device 103.

As illustrated in FIG. 17A, the camera 201 is a general imaging element and does not have a special structure as in the third modification example. Instead, the camera 201 outputs a frame timing pulse. The frame timing pulse is input to a light emission timing control unit 1701.

The light emission timing control unit 1701 synchronizes the light emission timings of the visible LED 1604 and the infrared LED 1605 with a frame timing pulse included in video data output by the camera 201 to control light emission of the visible LED 1604 and the infrared LED 1605 at a timing illustrated in FIG. 17B.

That is, the light emission timing control unit 1701 turn on only the visible LED 1604 at a first frame timing t1711, turns on only the infrared LED 1605 at a second frame timing t1712, and turns off both the visible LED 1604 and the infrared LED 1605 at a third frame timing t1713. This operation is repeated.

In addition, infrared LED turn-on captured video data obtained at the second frame timing and infrared LED turn-off captured video data obtained at the third frame timing are input to the infrared video acquisition unit 1702 (see FIG. 17C) formed in the input/output control unit 1201 of the video lighting processing device 103.

In addition, as illustrated in FIG. 17C, the infrared video acquisition unit 1702 includes an infrared LED turn-on captured video buffer 1703 that holds infrared LED turn-on captured video data, an infrared LED turn-off captured video buffer 1704 that holds infrared LED turn-off captured video data, and an adder 1705.

The infrared LED turn-on captured video data output from the infrared LED turn-on captured video buffer 1703 and the infrared LED turn-off captured video data output from the infrared LED turn-off captured video buffer 1704 are input to the adder 1705.

The adder 1705 subtracts the infrared LED turn-off captured video data from the infrared LED turn-on captured video data for each pixel. Then, the infrared LED turn-off captured video data, that is, a noise component due to visible light, which is included in the infrared LED turn-on captured video data is subtracted.

With the above configuration, although a frame rate is reduced to ⅓ as compared with the third modification example, an infrared image can be acquired by using the general-purpose camera 201 as it is. Thus, as in the third modification example, it is possible to prevent the occurrence of a medical accident that damages blood vessels in a surgical operation and expect an improvement in safety.

Further, by increasing the type of light that emits not only infrared light but also light having only a specific wavelength spectrum and performing the processing illustrated in FIGS. 17A, 17B, and 17C, it is possible to acquire video data having the specific wavelength spectrum.

As the video lighting processing device 103, a general personal computer can be used as it is. Thus, not only a multi-viewpoint video based on visible light of the operation field 106*a* and a multi-viewpoint video based on infrared light which displays blood vessels, but also information output by an external apparatus can be displayed on the display unit 1125 and the external monitor 104.

Fifth Modification Example: Variation of Fixing Instrument 102*b*

Figure 18:
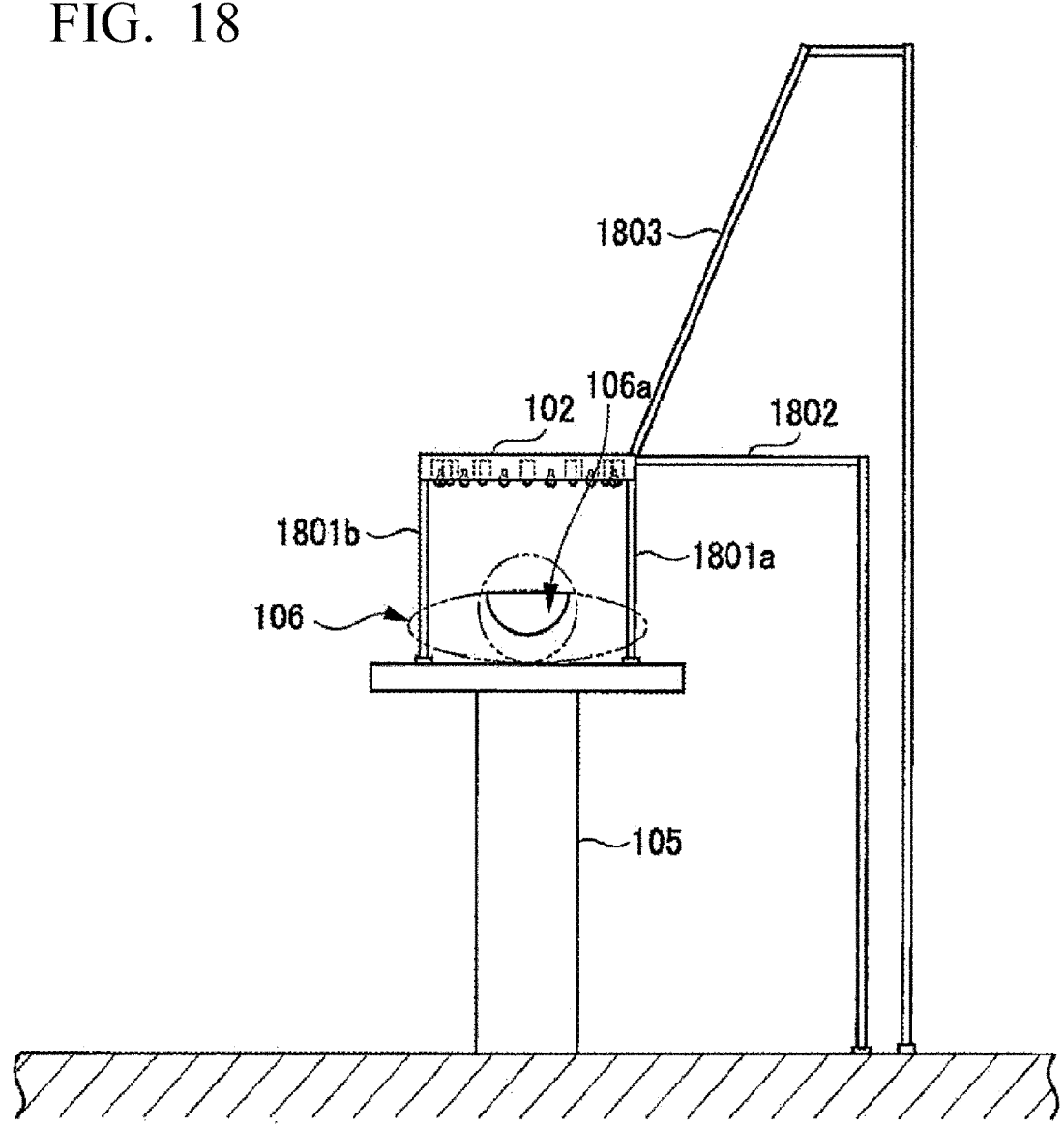
FIG. 18 is a schematic view illustrating a variation of a suspension arm according to a fifth modification example of the present invention.

FIG. 18 is a schematic view illustrating a variation of the fixing instrument 102*b* according to a fifth modification example of the present invention.

The fixing instrument 102*b* illustrated in FIG. 1 is provided to maintain a state where the imaging lighting instrument 102 is suspended from the operation field 106*a*.

The fixing instrument 102*b* is configured to be suspended from the ceiling of an operating room (not illustrated). As a result, the fixing instrument 102*b* does not interfere with medical treatment by the surgeon 107.

When a technical idea that does not interfere with medical treatment by the surgeon 107 is disregarded, as illustrated in FIG. 18, legs 1801*a* and 1801*b* extending directly below the imaging lighting instrument 102 and an extension arm 1802 extending directly beside the imaging lighting instrument 102 may also be provided. Further, an extension arm 1803 extending obliquely above the imaging lighting instrument 102 can also be provided. In this manner, various variations are conceivable as a method of a fixing instrument for maintaining a state where the imaging lighting instrument 102 is suspended from the operation field 106*a*.

Instruments required by the surgeon 107 in a direct-view operation in the related art include three instruments, that is, a shadowless lamp, an operation part imaging camera, and an information display device. These have traditionally existed separately.

An object of the multi-viewpoint video capturing device 101 according to the present invention is to provide various information essential for an operation to the surgeon 107 in an integrated manner, like a cockpit of an airplane.

For example, it is possible not only to share effective video information with a plurality of medical professionals in real time, but also to display preoperative simulation information such as CT images, MRI images, and 3D reconstructed images before an operation, navigation information such as appropriate blood vessel running of a main part based on infrared images, and the like on the external monitor 104 in an appropriate layout in accordance with the progress of the operation.

In addition, vital information of the patient 106 which is acquired in real time such as the blood pressure, pulse, electrocardiogram, and electroencephalogram of the patient 106, medical safety information such as an operative method and operation members, and medical cost information such as equipment to be used may be displayed as shared information.

In recent years, social demands for medical safety have increased significantly, and it is expected that the multi-viewpoint video capturing device 101 according to the embodiment of the present invention plays a major role in enhancing the safety of an operation.

For operations that have been performed so far only in a direct-view manner with the naked eye, various information such as live magnification information, infrared information, preoperative radiation image information, 3D simulation information, and medical safety information can be displayed to the surgeon 107 to significantly improve the safety of an operation.

In addition, by appropriately archive-recording enlarged live information, it is possible to contribute to the education of students and young surgeons and store it as a record that can withstand the disclosure of medical information.

In addition, although a shadowless lamp is an indispensable equipment in all operating rooms, the camera device with a light used in the embodiment of the present invention can serve as a more compact shadowless lamp. As a result, using the camera device with a light used in the present invention eliminates the need to install a large-scale shadowless lamp in an operating room, allowing the camera device to become a core facility in an operating room, of which there are approximately 20,000 throughout Japan.

As described above, the multi-viewpoint video capturing device 101 according to the embodiment of the present invention can be regarded as a completely new operation support system, and the multi-viewpoint video capturing device 101 may also have the potential to completely change the state of operating rooms around the world.

As described above, the present multi-viewpoint video capturing device is intended to be used mainly for surgical operations on living bodies, but the features of the present device that realizes a clear lighting environment in which blocking by the head or body of an operator does not occur, and operation filed video capturing that does not cause blocking cab be effectively applied in the fields of pathological anatomy, judicial anatomy, surgical anatomy, educational anatomy for corpses and also in veterinary surgery for animals.

Although the embodiment of the present invention has been described above, the present invention is not limited to the above-described embodiment and also includes other modification examples and application examples without departing from the gist of the present invention described in the claims.

For example, in the above-described embodiment, the configuration of the device and the system are described in detail and specifically in order to facilitate the understanding of the present invention, and it is not necessarily limited to including all of the configurations described.

Further, it is possible to replace a portion of a configuration of a certain embodiment with a configuration of another embodiment and to add a configuration of another embodiment to a configuration of a certain embodiment. In addition, it is also possible to perform addition, deletion, or replacement of another configuration for a portion of a configuration of each embodiment.

REFERENCE SIGNS LIST

101 Multi-viewpoint video capturing device
102 Imaging lighting instrument
102a Housing
102b Fixing instrument
103 Video lighting processing device
104 External monitor
105 Operating table
106 Patient
106a Operation field
107 Surgeon
201 Camera
202 Light
203 USB hub
401 Handle
601 Imaging lighting instrument
601a Housing
601b Fixing instrument
602 Imaging lighting instrument
602a First housing
602b First fixing instrument
602c Second housing
602d Second fixing instrument
701 Imaging lighting instrument
701a First housing
701b First fixing instrument
701c Second housing
701d Second fixing instrument
702 Imaging lighting instrument
702a Housing
702b Fixing instrument
801 Imaging lighting instrument
801a Housing
801b Fixing instrument
802 Imaging lighting instrument
802a Housing
802b Fixing instrument
901 Imaging instrument
901a Housing
1001 Lighting instrument
1001a Housing
1007 First camera
1008 Second camera
1101 Camera array unit
1102 Lighting array unit
1103 Network
1104 Microcomputer
1105 Multiplexer
R1106 Current limiting resistor
1107 Bus
1108 CPU
1109 ROM
1110 RAM
1111 Serial interface
1121 Bus
1122 CPU
1123 ROM
1124 RAM
1125 Display unit
1126 Operation unit 1127 Non-volatile storage
1128 Serial interface
1129 NIC
1201 Input/output control unit
1202 Camera calibration processing unit
1204 Presentation viewpoint gaze point determination processing unit
1205 Video processing unit
1206 Lighting determination processing unit
1207 Gaze point coordinates
1401 Multi-viewpoint video capturing device
1402 Imaging lighting instrument
1501 Multi-viewpoint video capturing device
1502 Imaging lighting instrument
1601 Imaging lighting instrument
1602 LED light
1603 Camera unit
1604 Visible LED
1605 Infrared LED
1606 Cold mirror
1701 Light emission timing control unit
1702 Infrared video acquisition unit
1703 Infrared LED turn-on captured video buffer
1704 Infrared LED turn-off captured video buffer
1705 Adder
1801a Leg
1802, 1803 Extension arm

What is claimed is:

1. A multi-viewpoint video capturing device comprising:
an imaging instrument including a plurality of cameras attached to a circular ring-shaped or arc-shaped housing made of a wire member of a finite length and aimed toward a subject being a target for work performed by an operator; and
a fixing instrument configured such that the imaging instrument is disposed at a position between the operator's head and the subject;
a camera calibration processing unit configured to estimate camera parameters including positions, postures, and focal lengths of the plurality of cameras attached to the imaging instrument, based on imaging information of the subject imaged by the plurality of cameras; and
a presentation viewpoint gaze point determination processing unit configured to detect a gaze point, which is a region of the subject perceived by the operator in multi-viewpoint image data, estimate three-dimensional coordinate information of the gaze point with reference to the camera parameters, and select one or a plurality of cameras that will perform imaging from a direction suitable for observation by the operator or an observer outside an operation field based on the three-dimensional coordinate information.

2. The multi-viewpoint video capturing device according to claim 1, wherein
the imaging instrument includes a plurality of lights, and
the plurality of lights are disposed between the plurality of cameras attached to the housing.

* * * * *